(12) United States Patent
Hock et al.

(10) Patent No.: US 9,242,240 B2
(45) Date of Patent: Jan. 26, 2016

(54) OLEFIN METATHESIS CATALYSTS AND RELATED METHODS

(71) Applicant: Massachusetts Institute of Technology, Cambridge, MA (US)

(72) Inventors: Adam S. Hock, Chicago, IL (US); Richard R. Schrock, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/479,917

(22) Filed: Sep. 8, 2014

(65) Prior Publication Data

US 2015/0065723 A1  Mar. 5, 2015

Related U.S. Application Data

(60) Division of application No. 13/735,635, filed on Jan. 7, 2013, now Pat. No. 8,829,219, which is a continuation of application No. 13/033,472, filed on Feb. 23, 2011, now Pat. No. 8,350,073, which is a continuation of application No. 11/603,951, filed on Nov. 22, 2006, now Pat. No. 7,932,397.

(51) Int. Cl.
*C07C 6/00* (2006.01)
*C07F 11/00* (2006.01)
(Continued)

(52) U.S. Cl.
CPC ............ *B01J 31/2295* (2013.01); *B01J 31/122* (2013.01); *B01J 31/181* (2013.01); *B01J 31/1805* (2013.01); *B01J 31/2234* (2013.01);
(Continued)

(58) Field of Classification Search
CPC ............... B01J 31/2291; B01J 31/2295; B01J 2531/64; C07C 6/04
USPC .............................. 585/646; 556/58; 548/109
See application file for complete search history.

(56) References Cited

U.S. PATENT DOCUMENTS 4,681,956 A * 7/1987 Schrock .......................... 556/12
4,727,215 A 2/1988 Schrock
(Continued)

OTHER PUBLICATIONS

Hock et al., Journal of American Chemical Society, vol. 128, No. 50, pp. 16373-16375 (Published on the Web Dec. 5, 2006).*
(Continued)

*Primary Examiner* — Porfirio Nazario Gonzalez
(74) *Attorney, Agent, or Firm* — Choate, Hall & Stewart, LLP; Brenda Herschbach Jarrell; Xiaodong Li

(57) ABSTRACT

The present invention provides methods for the synthesis of catalysts and precursors thereof. Methods of the invention may comprise combining a catalyst precursor and at least one ligand to generate a catalytically active species, often under mild conditions and in high yields. In some cases, a wide variety of catalysts may be synthesized from a single catalyst precursor. Methods of the invention may also include the preparation of catalysts which, under reaction conditions known in the art, may have been difficult or impossible to prepare and/or isolate due to, for example, steric crowding at the metal center. The present invention also provides catalyst compositions, and precursors thereof, which may be useful in various chemical reactions including olefin metathesis. In some cases, methods of the invention may reduce the number of synthetic and purification steps required to produce catalysts and/or other reaction products, as well as reducing time, cost, and waste production.

32 Claims, 5 Drawing Sheets

(51) Int. Cl.
*B01J 31/22* (2006.01)
*B01J 31/18* (2006.01)
*B01J 31/12* (2006.01)
*C07C 6/04* (2006.01)

(52) U.S. Cl.
CPC .......... *B01J 31/2265* (2013.01); *B01J 31/2291* (2013.01); *C07C 6/04* (2013.01); *B01J 2231/482* (2013.01); *B01J 2231/54* (2013.01); *B01J 2231/543* (2013.01); *B01J 2531/64* (2013.01); *B01J 2531/66* (2013.01); *C07C 2531/22* (2013.01)

(56) References Cited

U.S. PATENT DOCUMENTS

| | | | |
|---|---|---|---|
| 5,055,628 | A | 10/1991 | Lin et al. |
| 5,446,102 | A | 8/1995 | Oziomek et al. |
| 5,639,900 | A * | 6/1997 | Bell et al. ............ 556/57 |
| 5,889,128 | A | 3/1999 | Schrock et al. |
| 6,121,473 | A | 9/2000 | Schrock et al. |
| 6,271,325 | B1 | 8/2001 | McConville et al. |
| 6,316,555 | B1 | 11/2001 | Schrock et al. |
| 6,346,652 | B1 | 2/2002 | Schrock et al. |
| 6,610,806 | B2 | 8/2003 | Schrock et al. |
| 6,855,839 | B2 | 2/2005 | McConville et al. |
| 7,135,544 | B2 | 11/2006 | Schrock et al. |
| 7,932,397 | B2 * | 4/2011 | Hock et al. ............ 548/101 |
| 8,143,429 | B2 * | 3/2012 | Ochiai et al. ............ 556/43 |
| 8,222,469 | B2 | 7/2012 | Schrock et al. |
| 8,350,073 | B2 | 1/2013 | Hock et al. |
| 8,362,311 | B2 | 1/2013 | Schrock et al. |
| 8,546,500 | B2 | 10/2013 | Hoveyda et al. |
| 8,598,400 | B2 | 12/2013 | Hoveyda et al. |
| 8,829,219 | B2 | 9/2014 | Hock et al. |
| 9,073,801 | B2 | 7/2015 | Hoveyda et al. |
| 9,079,173 | B2 | 7/2015 | Schrock et al. |
| 9,085,595 | B2 | 7/2015 | Schrock et al. |
| 2011/0015430 | A1 | 1/2011 | Schrock et al. |
| 2011/0065915 | A1 | 3/2011 | Malcolmson et al. |
| 2011/0077421 | A1 | 3/2011 | Schrock et al. |
| 2011/0237815 | A1 | 9/2011 | Hock et al. |
| 2011/0245477 | A1 | 10/2011 | Hoveyda et al. |
| 2012/0323000 | A1 | 12/2012 | Hoveyda et al. |
| 2013/0116434 | A1 | 5/2013 | Schrock et al. |
| 2013/0274482 | A1 | 10/2013 | Schrock et al. |
| 2013/0281706 | A1 | 10/2013 | Hock et al. |
| 2014/0309388 | A1 | 10/2014 | Schrock et al. |
| 2014/0316088 | A1 | 10/2014 | Schrock et al. |
| 2014/0330018 | A1 | 11/2014 | Czirok et al. |
| 2014/0378637 | A1 | 12/2014 | Schrock et al. |
| 2015/0065723 | A1 | 3/2015 | Hock et al. |

OTHER PUBLICATIONS

Wampler et al., Organometallics, vol. 26, No. 26, pp. 6674-6680 (2007).*

Singh et al., Organometallics, vol. 26, No. 10, pp. 2528-2539 (2007).*

[No Author Listed] New catalysts promise faster, cleaner, and more efficient research platform. Science Daily. 2 pages. (Nov. 16, 2008).

Aeilts et al., A readily available and user-friendly chrial catalyst for efficient enantioselective olefin metathesis, Angew Chem Int Ed, 40(8):1452-1456 (2001).

Agbossou et al., Synthesis and Reactivity of Chiral Rhenium Alcohol Complexes of the Formula [(μ5-$C_5H_5$)Re(NO)($PPh_3$)(ROH)] ⊕ $BF4\Theta$. Chem Berichte,123(6):1293-1299 (1990).

Al Obaidi, N. et al., Steric and Electronic Effects on the Chemistry of Molybdenum Octahedrally Co-ordinated by Six Nitrogen Atoms. The Molecular Structure of [Mo{HB(3,5-Me2C3N2H)3)(NO)(pyrollide)2], J. Chem. Soc., Chem. Commun. 690-692 (1984).

Anderson, D. et al., Kinetic selectivity of olefin metathesis catalysts bearing cyclic (alkyl)(amino)carbenes. Organometallics, 27(4):563-566 (2008).

Ascenso, J. et al., Synthesis and characterization of [W(NC4Me4)2CI2] and [W(NC4Me4)2(CH3)2], the first azametal-locene tungsten complexes with pyrrolyl ligands. Electronic structure and bonding of tungsten bispyrrolyl complexes. lnorg Chem Acta, 356:249-258 (2003).

Bailey, B. et al., Evaluation of molybdenum and tungsten metathesis catalysts for homogeneous tandem alkane metathesis, Organometallics. 28(1):355-360 (2009).

Bazan, G. et al., Living ring-opening metathesis polymerization of 2, 3-difunctionalized 7-oxanorbornenes and 7-oxanorbornadienes by Mo(CHCMe$_2$R)(N-2,6-$C_6H_3$-iso-$Pr_2$)(O-tert-Bu)$_2$ and Mo(CHCMe$_2$R)(N-2,6-$C_6H_3$-iso-$Pr_2$)(OCMe$_2$CF$_3$)$_2$. J Am Chem Soc, 113(18):6899-6907 (1991).

Bei, X. et al., Highly efficient olefin-metathesis catalysts, Pharm Technol, s18 (2008).

Blackwell, H. et al., New approaches to olefin cross-metathesis. J Am Chem Soc., 122:58-71 (2000).

Blackwell, J. et al., Enediynes via sequential acetylide reductive coupling and alkyne metathesis: Easy access to well-defined molybdenum initiators for alkyne metathesis, Organometallics 22:3351-3353 (2003).

Blanc, F. et al., Dramatic Improvements of Well-Defined Silica Supported Mo-Based Olefin Metathesis Catalysts by Tuning the N-Containing Ligands. J. Am. Chem. Soc., 129(27):8434-8435 (2007).

Blanc, F. et al., Highly Active, Stable, and Selective Well-Defined Silica Supported Mo Imido Olefin Metathesis Catalysts, J. Am. Chem. Soc., 129(17):1044-1045 (2007).

Blanc, F. et al., Surface versus molecular siloxy ligands in well-defined olefin metathesis catalysis: [{(RO)$_3$SiO}Mo(=NAr)(=CH$_t$Bu)(CH$_2$tBu)], Angew. Chem. Int. Ed., 45:1216-1220 (2006).

Bornand, M. et al., Mechanism-based design of a ROMP catalyst for sequence-selective copolyerization, Angew Chem Int Ed Engl., 44(48):7909-7911 (2005).

Brunner, H et al., Optisch aktive Übergangsmetall-Komplexe, Li: P-Liganden als optisch aktive Hilfsstoffe in den Komplexen $C_5H_5$M(CO)(NO)L, M=Cr, Mo, W. Chem Ber., 11:673-691 (1978).—Abstract only.

Brunner, H. et al., Catalytic hydrosilylation or hydrogenation at one coordination site of Cp'Fe(CO)(X)] fragments, Angewandte Chemie Intl Ed Engl, 29(10):1131-1132 (1990).

Brunner, H., Optical activity at an asymmetrical manganese atom, Angew Chem. Int Ed Engl., 8:382-383 (1969).

Brunner, H., Optically active organometallic compounds of transition elements with chiral metal atoms, Angew Chemie Intl Ed., 38(9):1194-1208 (1999).

Brunner, H., Stability of the metal configuration in chiral-at-metal half-sandwich compounds, Eur J lnorg Chem., 905-912 (2001).

Burdett, K. et al., Renewable monomer feedstocks via olefin metathesis: fundamental mechanistic studies of methyl oleate ethenolysis with the first-generation grubbs catalyst, Organometallics, 23(9):2027-2047 (2004).

Cantrell, G. et al., Ring-Opening Metathesis of a Cyclic Imine, Organometallics, vol. 19:3562-3568 (2000).

Chatterjee, A. et al., Olefin Cross-Metathesis, Handbook Metathesis, 2:246-295 (2003).

Connon, S. et al., Recent developments in olefin cross-metathesis, Angew Chem Int Ed Engl, 42(17):1900-1923 (2003).

Corma, A. et al., Chemical routes for the transformation of biomass into chemicals, Chem Rev, 107(6):2411-502 (2007).

Dias, A. et al., Synthesis, characterisation, crystal structure, reactivity and bonding in titanium complexes containing 2,3,4,5-tetramethylpyrrolyl. J. Chem. Soc., Dalton Trans.1055-1061 (1997).

Dinger, M. et al., High turnover numbers with ruthenium-based metathesis catalysts, Adv Synth Catal, 344(6-7):671-677 (2002).

Dolman, S. et al., Efficient catalytic enantioselective synthesis of unsaturated amines: preparation of small- and medium-ring cyclic amines through mo-catalyzed asymmetric ring-closing metathesis in the absence of solvent, J Am Chem Soc., 124(24):6991-6997 (2002).

Dolman, S., New chiral molybdenum metathesis catalysts; application of the enantioselective preparation of cyclic amines, Ph.D. Thesis. MIT., 234 pages, (Jun. 2004).

(56) References Cited

OTHER PUBLICATIONS

Duarte, M. et al., Chlorobis(dimethylamido)(η5-2,5-dimethylpyrrolyl)titanium(IV), [Ti(NMe$_2$)$_2$(DMP)Cl], Acta Cryst. C., 61:104-106 (2005).
Feldman, J. et al., Recent advances in the schnistry of "d0" alkylidine metallacyclobutane complexes, Prog. lnorg. Chem., 39:1-74 (1991).
Flook, M. et al., Z-selective olefin metathesis processes catalyzed by a molybdenum hexaisopropylterphenoxide monopyrrolide complex, J. Am Chem Soc., 131(23):7962-7963 (2009).
Fontecave, M. et al., Chiral-at-metal complexes as asymmetric catalysts, In Chiral Diazaligands for Asymmetric Synthesis, Top Organometallic Chem,15:271-288 (2005).
Forman, G. et al., A stable ruthenium catalyst for productive olefin metathesis, Organometallics, 23(21):4824-4827 (2004).
Fürstner, A. et al., Alkyne metathesis: Development of a novel molybdenum-based catalyst system and its application to the total synthesis of Epothilone A and C, Chem. Eur. J., 7(24):5299-5317 (2001).
Fürstner, A. et al., Cationic ruthenium allenylidene complexes as catalysts for ring closing olefin metathesis, Chemistry, 6(10):1847-1857 (2000).
Fürstner, A. et al., Mo[N(t-Bu)(Ar)]$_3$ complexes as catalyst precursors: in situ activation and application to metathesis reactions of alkynes and diynes, J. Am. Chem. Soc, 121: 9453-9454 (1999).
Ganter, C., Chiral organometallic half-sandwich complexes with defined metal configuration, Chem Soc Rev., 32(3):130-138 (2003).
Giessert, A. et al., Intermolecular enol ether-alkyne metathesis, Org Lett., 5(10):1793-1796 (2003).
Gillingham, D. et al., Chiral N-heterocyclic carbenes in natural product synthesis: application of Ru-catalyzed asymmetric ring-opening/cross-metathesis and Cu-catalyzed allylic alkylation to total synthesis of baconipyrone C, Angew Chem Int Ed Engl., 46(21):3860-3864 (2007).
Giudici, R. et al., Directed catalytic asymmetric olefin metathesis. Selectivity control by enoate and ynoate groups in Ru-catalyzed asymmetric ring-opening/cross-metathesis, J Am Chem Soc, 129(13):3824-3825 (2007).
Hadlington, S., Catalyst flexes for extra control, Chemistry World, Nov. 17, 2008. Last accessed online, Dec. 1, 2008.
Hesek D. et al., The first asymmetric synthesis of chiral ruthenium tris(bipyridine) from racemic ruthenium bis(bipyridine) complexes, Tetrahedron Lett, 41(15):2617-2620 (2000).
Hock, A. et al., Dipyrrolyl Precursors to Bisalkoxide Molybdenum Olefin Metathesis Catalysts, J. Am. Chem. Soc., 128(50):16373-16375 (2006).
Ibrahem, I. et al., Highly Z- and enantioselective ring-opening/cross-metathesis reactions catalyzed by stereogenic-at-Mo adamantylimido complexes, J Am Chem Soc., 131(11):3844-3845 (2009).
International Preliminary Report on Patentability from International Patent Application Serial No. PCT/US2007/024318, filed Nov. 21, 2007, mailed May 26, 2009.
International Preliminary Report on Patentability in connection with Application Serial No. PCT/US2009/000465 issued Jul. 27, 2010.
International Search Report and Written Opinion in connection with Application Serial No. PCT/US2009/000465 mailed Jul. 13, 2009.
International Search Report and Written Opinion in PCT/US2007/024318, mailed on May 7, 2008.
Invitation to Pay Additional Fees in connection with Application Serial No. PCT/US2009/000465 mailed May 11, 2009.
Jiang, A. et al., Fundamental studies of tungsten alkylidene imido monoalkoxidepyrrolide complexes, J Am Chem Soc., 131(22):7770-7780 (2009).
Jiang, A. et al., Highly Z-selective metathesis homocoupling of terminal olefins, J Am Chem Soc., 131(46):16630-16631 (2009).
Kershner, D. et al., η5-Heterocyclic Metal Carbonyls, Coord. Chem. Rev., 79:279-292 (1987).
Kiely A. et al., Enantioselective synthesis of medium-ring heterocycles, tertiary ethers, and tertiary alcohols by Mo-catalyzed ring-closing metathesis, J Am Chem Soc., 124(12):2868-2869 (2002).
Knof, U. et al., Predetermined chirality at metal centers, Angew Chemie Intl Ed., 38(3):302-322 (1999).
Kreickmann, T. et al., Imido Alkylidene Bispyrrolyl Complexes of Tungsten, Organometallics, 26:5702-5711 (2007).
Lacour, J. et al., Recent developments in chiral anion mediated asymmetric chemistry, Chem Soc Rev, 32(6):373-382 (2003).
Lee, A. et al., Enantioselective synthesis of cyclic enol ethers and all-carbon quaternary stereogenic centers through catalytic asymmetric ring-closing metathesis, J Am Chem Soc., 128(15):5153-5157 (2006).
Lee, Y. et al., Endo-selective enyne ring-closing metathesis promoted by stereogenic-at-Mo monoalkoxide and monoaryloxide complexes. Efficient synthesis of cyclic dienes not accessible through reactions with Ru carbenes, J Am Chem Soc., 131(30):10652-10661 (2009).
Liu, Z. et al., Regioselective ring-opening/cross-metathesis reactions of norbornene derivatives with lectron-rich olefins, Org Lett. 7(I):131-133 (2005).
Lokare, K. et al., Synthesis, properties, and structure of tethered molybdenum alkylidenes, Organometallics, 27(19):5130-5138 (2008).
Malcolmson, S. et al., Highly efficient molybdenum-based catalysts for enantioselective alkene metathesis, Nature, 456(7224):933-937 (2008).
Marinescu, S. et al., Ethenolysis reactions catalyzed by imido alkylidene monoaryloxide monopyrrolide (MAP) complexes of molybdenum, J Am Chem Soc, 131(31):10840-10841 (2009).
Marinescu, S. et al., Inversion of configuration at the metal in diastereomeric imido alkylidene monoaryloxide monopyrrolide complexes of molybdenum, J Am Chem Soc., 131(1):58-59 (2009).
Maruoka, K. et al., Efficient synthesis of sterically hindered chiral binaphthol derivatives, Bull Chem Soc Jpn, 61(8):2975-2976 (1988).
McDougal, N. et al., Asymmetric Morita-Baylis-Hillman reactions catalyzed by chiral Brønsted acids, J Am Chem Soc., 125(40):12094-12095 (2003).
McDougal, N. et al., The development of the asymmetric morita-baylis-hillman reaction catalyzed by chiral brønsted acids, Adv Synth Cat., 346:1231-1240 (2004).
Meek, S. et al., The significance of degenerate processes to enantioselective olefin metathesis reactions promoted by stereogenic-at-Mo complexes, J Am Chem Soc., 131(45):16407-16409 (2009).
Monchaud, D. et al., Ion-pair-mediated asymmetric synthesis of a configurationally stable mononuclear tris(diimine)-iron(II) complex, Angew Chem Int Ed Engl, 41(13):2317-2319 (2002).
Nicolaou, K. et al Metathesis reactions in total synthesis, Angew Chem Int Ed Engl., 44(29):4490-4527 (2005).
Pezet, F. et al., Highly diastereoselective preparation of ruthenium bis(diimine) sulfoxide complexes: new concept in the preparation of optically active octahedral ruthenium complexes, Organometallics, 19(20):4008-4015 (2000).
Poater, A. et al., Understanding d(0)-olefin metathesis catalysts: which metal, which ligands? J Am Chem Soc., 129(26):8207-8216 (2007).
Rhers, B. et al., A well-defined, silica-supported tungsten imido alkylidene olefin metathesis catalyst. Organometallics. 25, 3554-3557 (2006).
Sattely, E et al., Enantioselective synthesis of cyclic amides and amines through mo-catalyzed asymmetric ring-closing metathesis, J Am Chem Soc, 127(23):8526-8533 (2005).
Sattely, E. et al., Design and stereoselective preparation of a new class of chiral olefin metathesis catalysts and application to enantioselective synthesis of quebrachamine: catalyst development inspired by natural product synthesis, J Am Chem Soc.,131(3):943-953 (2009).
Sattely, E., Cyclic amines and amides through molybdenum-catalyzed asymmetric olefin metathesis: A total synthesis of quebrachamine. Boston College Dissertations and Theses. Paper AAI3256831. http://escholarship.bc.edu/dissertations/AA13256831, 340 pages. (Jan. 1, 2007).
Schrock, R. et al., Further studies of imido alkylidene complexes of tungsten, well-characterized olefm metathesis catalysts with controllable activity, Organometallics, 9(8):2262-2275 (1990).

(56) References Cited

OTHER PUBLICATIONS

Schrock, R. et al., Molybdenum alkylidyne complexes that contain 3,3'-di-t-butyl-5,5', 6,6'-tetramethyl-1, 11-biphenyl-2,21-diolate ([Biphen]$^{2-}$) ligand. J. Organomet, Chem. 684, 56-67 (2003).

Schrock, R. et al., Molybdenum and tungsten imido alkylidene complexes as efficient olefinmetathesis catalysts. Angew. Chem. Int. Ed. 42, 4592-4633 (2003).

Schrock, R. et al., Preparation of molybdenum and tungsten neopentylidyne complexes of the type M(CCMe$_3$)(O$_2$CR)$_3$, their reactions with acetylenes, and the X-ray structure of the $\mu_3$—cyclopropenyl complex W[C$_3$(CMe$_3$)Et$_2$]O$_2$CCH$_3$)$_3$. Organometallics. 5:25-33 (1986).

Schrock, R. et al., Synthesis of Molybdenum Imido Alkylidene Complexes and Some Reactions Involving Acyclic Olefins. J. Am. Chem. Soc., 112:3875-3886 (1990).

Schrock, R. et al., Thousands of catalysts for olefin metathesis: variability, longevity and asymmetry at the metal. Abstract. Presented at Technical University of Berlin (Oct. 24, 2008).

Schrock, R., High oxidation state multiple metal-carbon bonds. Chem. Rev.102, 145-179 (2002).

Schrock, R., Recent advances in high oxidation state Mo and W imido alkylidene chemistry. Chem Rev., 109(8):3211-26 (2009).

Schrodi, Y. et al., Ruthenium olefin metathesis catalysts for the ethenolysis of renewable feedstocks. Clean: Soil, Air, Water. 36:669-673 (2008).

Singh, R. et al., Molybdenum Imido Alkylidene Metathesis Catalysts That Contain Electron-Withdrawing Biphenolates or Binaphtholates. Organometallics. 26(10), 2528-2539 (2007).

Singh, R. et al., Synthesis of Monoalkoxide Monopyrrolyl Complexes Mo(NR)(CHR')(OR'')(pyrrolyl): Enyne Metathesis with High Oxidation State Catalysts. J. Am. Chem. Soc.129(42), 12654-12655 (2007).

Sinha, A. et al., Diphenylamido precursors to bisalkoxide molybdenum olefin metathesis catalysts. Organometallics. 25, 4621-4626 (2006).

Sinha, A. et al., Reactions of M(N-2,6-i-Pr$_2$C$_6$H$_3$)(ChR)(CH$_2$R')$_2$ (M=Mo, W) Complexes with Alcohols to Give Olefin Metathesis Catalysts of the Type M(N-2,6-i-Pr$_2$C$_6$H$_3$)(ChR)(CH$_2$R')(OR''). Organometallics. 25, 1412-1423 (2006).

Solans-Monfort, X. et al., d0 Re-based olefin metathesis catalysts, Re($\equiv$CR)($=$CHR)(X)(Y): The key role of X and Y ligands for efficient active sites, J Am Chem Soc,127(40):14015-14025 (2005).

Takano, S. et al., Enantioselective route to both (+)- and (−)-enantiomers of quebrachamine using a single chiral synthon. J Chem Soc Chem Commun. 1153-1155 (1981).

Takemura, H. et al., Stereochemical aspects of asymmetric Diels-Alder reaction catalyzed by chiral alkoxyaluminum dichlorides, Tetrahedron Lett, 28(46):5687-5690 (1987).

Tallarico, J. et al., Selectivity in ring-opening metatheses, Tetrahedron, 53(48):16511-16520 (1997).

Tayama, E. et al., Activation of ether functionality of allyl vinyl ethers by chiral bis(organoaluminum) Lewis acids: application to asymmetric Claisen rearrangement, Tetrahedron, 58(41):8307-8312 (2002).

Tonzetich, Z. et al., Reaction of Phosphoranes with Mo(N-2,6-i Pr$_2$C$_6$H$_3$)(CHCMe$_3$)[OCMe(CF$_3$)$_2$]$_2$: Synthesis and Reactivity of an Anionic Imido Alkylidyne Complex. Organometallics. 25, 4301-4306 (2006).

Totland, K. et al., Ring Opening Metathesis Polymerization with Binaptholate or Biphenolate Complexes of Molybdenum, Macromolecules (29): 6114-6125 (1996).

Tsai, Y. et al, Facile synthesis of trialkoxymolybdenum(VI) alkylidyne complexes for alkyne metathesis. Organometallics. 19, 5260-5262 (2000).

Van Veldhuizen, J. et al., A readily available chiral Ag-based N-heterocyclic carbene complex for use in efficient and highly enantioselective Ru-catalyzed olefin metathesis and Cu-catalyzed allylic alkylation reactions. J Am Chem Soc.127(18):6877-6882 (2005).

Van Veldhuizen, J. et al., A recyclable chiral Ru catalyst for enantioselective olefin metathesis. Efficient catalytic asymmetric ring-opening/cross metathesis in air. J Am Chem Soc. 2002 May 8;124(18):4954-4955. Erratum in: J Am Chem Soc.125(41):12666 (2003).

Walls, F. et al., Alkaloids from stemmadenia species-I: The alkaloids of S. Donnell-Smithii and S. Galeottiana, Tetrahedron, 2(3-4):173-82 (1958).

Weatherhead, G. et al., Mo-catalyzed asymmetric olefin metathesis in target-oriented synthesis: enantioselective synthesis of (+)-africanol, Proc Natl Acad Sci U S A, 101(16):5805-5809 (2004).

Werner, A. et al., Bur Kennfnie dee asymmetrimhen Kobaltatoms. I. Ber Dtsch Chem Ges. 44:1887-1898. German. (1911).

Yashiro, M. et al., Efficient stereochemical regulation of octahedral cobalt(III) complexes by a chiral bidentate ligand. Part 2. Remarkable effect of the chelate-ring size in the stereoselective formation of sym-cis-(ethylenediamine-N,N'-diacetato)(pentane-2,4-diamine)cobalt(III). J Chem Soc. Dalton Trans, 10:1511-1516 (1994).

Yashiro, M. et al., Efficient stereochemical regulation of octahedral cobalt(III) complexes by a chiral bidentate ligand. Part I. Effect of N-alkyl substitutions. J Chem Soc, Dalton Trans, 7:1073-1077 (1994).

Yi, C. et al., The ruthenium acetylide catalyzed cross-coupling reaction of terminal and internal alkynes: isolation of a catalytically active β-agostic intermediate species. Organometallics, 17(15):3158-3160 (1998).

Zhang, W. et al., A reductive recycle strategy for the facile synthesis of molybdenum(VI) alkylidyne catalysts for alkyne metathesis. Chem. Commun. 832-833 (2003).

Zhou et al., Synthesis and reactivity of chiral rhenium indenyl complexes of the formula [(η5 C9H7)Re(NO)(PPh3)(X)]n+. Organometallics.12(10);3918-23 (1993).

Zhu et al., Chiral Mo-Binol complexes: activity, synthesis, and structure. efficient enantioselective six-membered ring synthesis through catalytic metathesis. J Am Chem Soc. 121:8251-9 (1999).

* cited by examiner

OLEFIN METATHESIS CATALYSTS AND RELATED METHODS

CROSS-REFERENCE TO RELATED APPLICATIONS

This application is a Division of U.S. patent application Ser. No. 13/735,635, filed Jan. 7, 2013, now U.S. Pat. No. 8,829,219, which is a Continuation of U.S. patent application Ser. No. 13/033,472, filed Feb. 23, 2011, now U.S. Pat. No. 8,350,073, which is a Continuation of U.S. patent application Ser. No. 11/603,951, filed Nov. 22, 2006, now U.S. Pat. No. 7,932,397, the entirety of each of which is hereby incorporated by reference.

STATEMENT REGARDING FEDERALLY SPONSORED RESEARCH OR DEVELOPMENT

This invention was made with government support under Grant No. R01 GM059426 awarded by the National Institutes of Health and under Grant Nos. CHE0138495 and CHE0554734 awarded by the National Science Foundation. The government has certain rights in the invention.

FIELD OF THE INVENTION

The present invention generally relates to compositions useful as organometallic catalysts, and related methods.

BACKGROUND OF THE INVENTION

Transition metal-catalyzed reactions which form carbon-carbon bonds have become an important tool in synthetic organic chemistry. One example is transition metal-catalyzed olefin metathesis, which has been shown to be useful in the synthesis of high molecular weight polymers, pharmaceuticals, and other materials. Olefin metathesis may be defined conceptually as a mutual exchange of alkylidene units between two olefins involving both the formation and cleavage of carbon-carbon double bonds, i.e., via [2+2] cycloadditions between an M=C center and a carbon-carbon double bond. Metal alkylidene complexes including ruthenium and molybdenum alkylidene complexes have been shown to perform olefin metathesis in the presence of a variety of functional groups. However, in many cases, multi-step syntheses are required to generate the catalyst compositions.

In some applications, variation of the substituents and/or ligands of the catalyst may greatly affect the performance of the catalyst. For example, in asymmetric olefin metathesis, the stereoselectivity of a catalyst may be largely affected by the steric size and/or electronic properties of, for example, ligands bound to the metal center of the catalyst. Thus, the availability of a wide variety of catalysts, each having different combinations of ligands and/or substitutents, may be advantageous in optimizing catalysts and/or reactions conditions for a particular chemical reaction. However, using methods currently known in the art, the synthesis and isolation of many different catalyst compositions may be impractical. In some cases, the substitution or replacement of ligands bound to an organometallic catalyst may occur slowly and/or incompletely, or not all. In other cases, the synthesis of organometallic catalysts may occur with poor yield due to the occurrence of side reactions. For example, the syntheses of metal alkylidene complexes for olefin metathesis may often result in low yields due to competitive side reactions including deprotonation of the alkylidene.

Accordingly, improved methods are needed.

SUMMARY OF THE INVENTION

The present invention relates to compositions of matter comprising compounds having the structure,

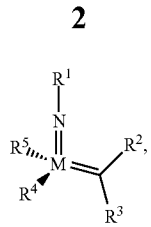

wherein M is Mo or W; $R^1$ is alkyl, heteroalkyl, aryl, or heteroaryl, optionally substituted; $R^2$ and $R^3$ can be the same or different and are hydrogen, alkyl, heteroalkyl, aryl, or heteroaryl, optionally substituted; $R^4$ and $R^5$ can be the same or different and are heteroalkyl or heteroaryl, optionally substituted, or $R^4$ and $R^5$ are joined together to form a bidentate ligand with respect to M, optionally substituted; and wherein $R^4$ and $R^5$ each comprise at least one nitrogen atom.

The present invention also provides methods for synthesizing a catalyst comprising providing a compound having the structure,

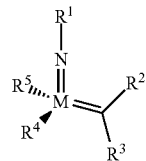

wherein M is Mo or W; $R^1$ is alkyl, heteroalkyl, aryl, or heteroaryl, optionally substituted; $R^2$ and $R^3$ can be the same or different and are hydrogen, alkyl, heteroalkyl, aryl, or heteroaryl, optionally substituted; $R^4$ and $R^5$ can be the same or different and are heteroalkyl or heteroaryl, optionally substituted, or $R^4$ and $R^5$ are joined together to form a bidentate ligand with respect to M, optionally substituted; and wherein $R^4$ and $R^5$ each comprise at least one nitrogen atom; and reacting the compound with an oxygen-containing ligand such that the oxygen-containing ligand replaces $R^4$ and $R^5$ to form a catalyst.

The present invention also provides methods for forming and using a catalyst comprising providing a catalyst precursor comprising an organometallic composition including a first nitrogen-containing ligand in a reaction vessel; replacing the first, nitrogen-containing ligand with a second, oxygen-containing ligand thereby synthesizing the catalyst, at a temperature of less than 100° C. and with a yield of at least 50%, in the reaction vessel; and catalyzing a reaction in the reaction vessel with the catalyst, wherein the catalyst is present at a concentration of less than 100 mM.

DETAILED DESCRIPTION

Figure 1:
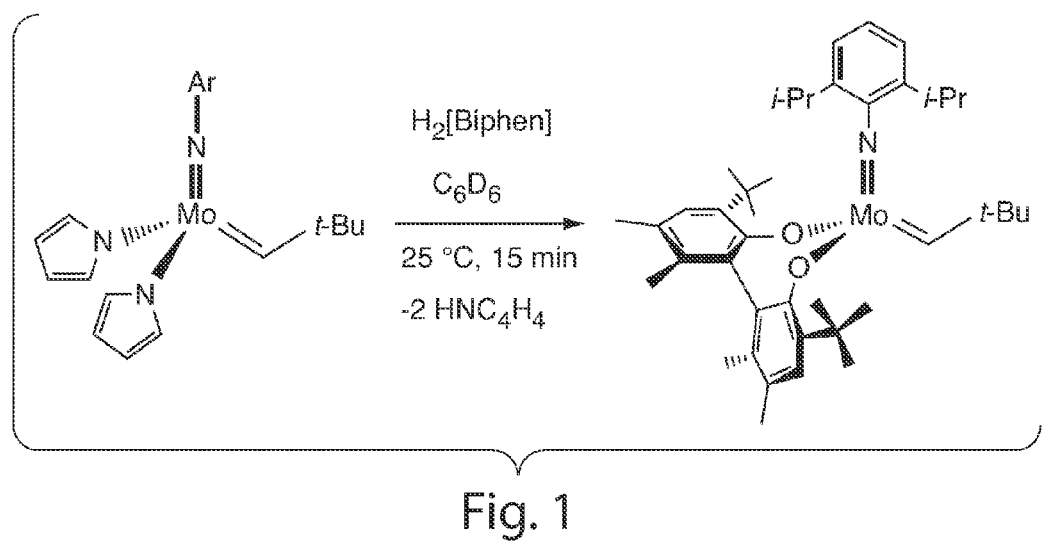
FIG. 1 shows the synthesis of a catalyst, according to one embodiment of the invention.

The present invention generally relates to organometallic compositions useful as catalysts and catalyst precursors, and related methods.

In some embodiments, the present invention provides methods for the synthesis of catalysts and precursors thereof. Methods of the invention may comprise combining a catalyst precursor and at least one ligand to generate a catalytically active species, often under mild conditions and in high yields. In some cases, a wide variety of catalysts may be synthesized from a single catalyst precursor. Methods of the invention may also include the preparation of catalysts which, under reaction conditions known in the art, may have been difficult or impossible to prepare and/or isolate due to, for example, steric crowding at the metal center. The present invention also provides catalyst compositions, and precursors thereof, which may be useful in various chemical reactions including olefin metathesis. In some cases, methods of the invention may reduce the number of synthetic and purification steps required to produce catalysts and/or other reaction products, as well as reducing time, cost, and waste production.

The present invention may advantageously provide methods for the rapid synthesis of a wide range of catalyst compositions, in some cases, in yields greater than 95%. The ability to synthesize catalysts rapidly and in high yields may be useful for the screening of known, as well as new, catalysts to determine the optimal conditions and/or reagents for a particular chemical reaction. In some cases, a catalyst precursor may be used to generate a large number of catalyst structures in which the ligands and/or ligand substitutents are varied. For example, the present invention may be utilized in the preparation of organometallic compositions useful as olefin metathesis catalysts, wherein the compositions comprise imido, alkoxide, and/or alkylidene ligands. A library of such catalysts having varied imido, alkoxide, and/or alkylidene ligands may be prepared and then appropriately screened to optimize catalyst performance for a given reaction.

Methods of the invention may also be useful for synthesizing catalyst structures that may be difficult to prepare using known methods. For example, olefin metathesis catalysts comprising one or more sterically large ligands may be prepared in high yields using the methods described herein, whereas such catalysts may only be prepared in low yields, or not at all, due to steric crowding at the metal center using known methods. In some cases, the present invention may also provide one-pot procedures involving the formation of a catalyst and subsequent use of the catalyst in a chemical reaction. The term "one-pot" reaction is known in the art and refers to a chemical reaction which can produce a product in one step which may otherwise have required a multiple-step synthesis. One-pot procedures may eliminate the need for isolation (e.g., purification) of catalysts and/or intermediates, while reducing the number of synthetic steps and the production of waste materials (e.g., solvents, impurities). This may also be advantageous in cases where relatively unstable catalysts may be needed for catalytic purposes.

Accordingly, in some embodiments, the present invention provides various compositions including organometallic compositions useful as catalyst precursors. As used herein, a "catalyst precursor" may refer to a chemical species which, upon activation, may produce an active catalyst species in a reaction. For example, an organometallic composition may comprise a first ligand which, upon activation, may be replaced with a second ligand to generate the catalytically active species. The activation step may comprise exposure of the catalyst precursor to, for example, an oxygen-containing ligand or other species. As shown in the illustrative embodiment shown in FIG. 1, a catalyst precursor comprising two pyrrolyl ligands may be activated to form a catalyst comprising a biphenolate ligand. In some cases, a single catalyst precursor may be activated to generate a wide variety of catalysts, often in high yields. The catalyst precursor may be isolated as a stable compound and, in some cases, may be converted in situ into the active form of the catalyst. As used herein, the term "catalyst" includes active forms of the catalyst participating in the reaction. In some embodiments, catalyst precursors of the invention may be advantageous in that the chemical composition, amount, and/or release of the catalytically active species may be controlled.

In some cases, the present invention provides catalyst precursors comprising compounds having the structure,

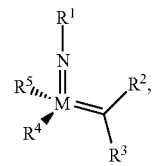

wherein M is Mo or W; $R^1$ is alkyl, heteroalkyl, aryl, or heteroaryl, optionally substituted; $R^2$ and $R^3$ can be the same or different and are hydrogen, alkyl, heteroalkyl, aryl, or heteroaryl, optionally substituted; $R^4$ and $R^5$ can be the same or different and are heteroalkyl or heteroaryl, optionally substituted, or $R^4$ and $R^5$ are joined together to form a bidentate ligand with respect to M, optionally substituted; and wherein $R^4$ and $R^5$ each comprise at least one nitrogen atom. In some cases, M is Mo.

In some embodiments, $R^4$ and $R^5$ can be the same or different and are heteroaryl groups comprising at least one nitrogen ring atom. In some cases, $R^4$ and $R^5$ each coordinate M via a nitrogen atom. For example, $R^4$ and $R^5$ may both be pyrrolyl groups which coordinate the metal via the nitrogen atoms of the pyrrolyl ring. $R^4$ and $R^5$ may comprise other heteroaryl or heteroalkyl groups, or $R^4$ and $R^5$ may be joined to form a bidentate ligand, such as a biphenolate or binaphtholate group. In some cases, at least one of $R^4$ and $R^5$ is a chiral ligand, or $R^4$ and $R^5$ are joined together to form a chiral ligand.

In some embodiments, at least one of $R^2$ and $R^3$ may be hydrogen, such that, when $R^2$ is hydrogen, $R^3$ may be alkyl, heteroalkyl, aryl, or heteroaryl, optionally substituted, or, when $R^3$ is hydrogen, $R^2$ is alkyl, heteroalkyl, aryl, or heteroaryl, optionally substituted. In some embodiments, M is Mo; $R^1$ is substituted aryl; $R^2$ is alkyl, optionally substituted; $R^3$ is hydrogen; $R^4$ and $R^5$ are heteroaryl, optionally substituted, or $R^4$ and $R^5$ are joined together to form a bidentate ligand with respect to M, optionally substituted; and wherein $R^4$ and $R^5$ each comprise at least one nitrogen atom.

Figure 2:
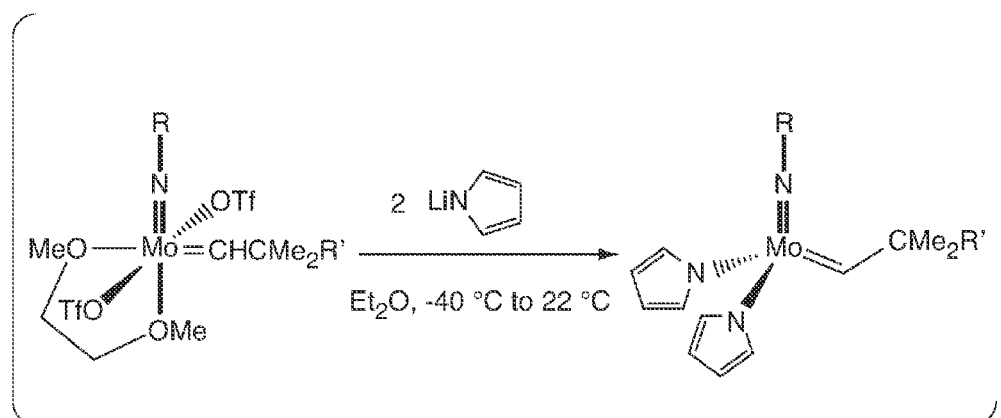
FIG. 2 shows the synthesis of a catalyst precursor, according to one embodiment of the invention.

The catalyst precursors may be synthesized according to various methods known in the art. In an illustrative embodiment shown in FIG. 2, the catalyst precursor may be synthesized by the addition of lithium pyrrolide to a mixture of Mo(NR$^1$)(CHCMe$_2$R')—(OTf)$_2$(dimethoxyethane), wherein R' is alkyl, heteroalkyl, aryl, heteroaryl, or substituted derivatives thereof. The reaction may proceed iii high yield (e.g., >95% in some cases) with little or substantially no side reactions, such as the deprotonation of alkylidene to give an alkylidyne. The synthesis of the catalyst precursor may be conducted in the presence of various organic solvents, including diethyl ether, dichloromethane, and the like. In one set of embodiments, dimeric dipyrrolyl complexes, {Mo(NR$^1$)(CHCMe$_2$RD(NC$_4$H$_4$)$_2$}$_2$, can be prepared readily and in good yield from Mo(NR$^1$)(CHCMe$_2$R')(OTf)$_2$(DME) species.

The present invention also provides methods for generation of catalyst, including homogeneous catalysts and heterogeneous catalysts. In some cases, the catalyst may be generated in situ to catalyze a chemical reaction, as described more fully below. Methods for synthesizing the catalyst may comprise providing a catalyst precursor comprising an organometallic composition including a first nitrogen-containing ligand. The first, nitrogen-containing ligand may be replaced with a second, oxygen-containing ligand, thereby synthesizing the catalyst. As shown by the illustrative embodiment in Scheme 1, the method may comprise providing a catalyst precursor as described herein and reacting the catalyst precursor with an oxygen-containing ligand (e.g., R$^6$ and R$^7$) such that the oxygen-containing ligand replaces R$^4$ and R$^5$ to form the catalyst, wherein R$^4$ and R$^5$, in protonated or non-protonated form, may be released. R$^6$ and R$^7$ may be oxygen-containing ligands or R$^6$ and R$^7$ may be joined together to form a bidentate, oxygen-containing ligand. In some cases, the oxygen-containing ligand may be in a protonated form prior to coordinating the metal center, and may then have sufficiently ionic character (e.g., may be deprotonated) upon coordination to the metal center. Similarly, the nitrogen-containing ligand may be in a deprotonated form when bound to the metal center, and may become protonated upon release from the metal center. For example, R$^4$ and R$^5$ may be pyrrolyl groups coordinating the metal center such that, upon exposure of the catalyst precursor to an oxygen-containing ligand such as biphenolate, the biphenolate ligand may replace the pyrrolyl groups to form the catalyst, resulting in the release of two equivalents of pyrrole. Ligands of the present invention may be described using nomenclature consistent with their protonated or deprotonated forms, and, in each case, it should be understood that the ligand will adopt the appropriate form to achieve its function as, for example, either a ligand bound to a metal center or an inert species in the reaction mixture. For example, in an illustrative embodiment, the term "pyrrolyl" may be used to describe a deprotonated, anionic pyrrole group which may coordinate a metal center, while the term "pyrrole" may be used to describe a neutral pyrrole group which does not coordinate the metal center but may be present in solution as an inert species that does not react with other components in the reaction mixture.
Scheme 1

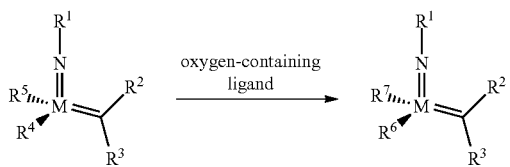

The synthesis of catalysts having the structure, Mo(NR$^1$)(CHR$^2$R$^3$)(R$^6$)(R$^7$), from catalyst precursors having the structure, Mo(NR$^1$)(CHR$^2$R$^3$)(R$^4$)(R$^5$), may require that both R$^4$ and R$^5$ groups, or a bidentate ligand formed by joining R$^4$ and R$^5$, be replaced readily with R$^6$ and R$^7$, or a bidentate ligand formed by joining R$^6$ and R$^7$. In some cases, R$^4$ and R$^5$ may be selected such that, upon release of the R$^4$ and R$^5$ groups, the released R$^4$ and R$^5$ groups may not interfere with subsequent reactions that may involve the catalyst or may not react with any other species in the reaction. In some cases, the R$^4$ and R$^5$ groups may be released in protonated form (e.g., H—R$^4$ and H—R$^5$, or H$_2$(R$^4$—R$^5$)) but may be similarly inert to other species or reagents, including those involved in subsequent reactions.

Those of ordinary skill in the art would be able to select the appropriate nitrogen-containing ligand(s) (e.g., R$^4$ and R$^5$) suitable for use in a particular application. For example, a one-pot synthesis may be performed to generate a catalyst and to carry out a chemical reaction using the catalyst, wherein, upon in situ generation of the catalyst, the released nitrogen-containing ligand(s) do not react with reagents of the chemical reaction and/or other components of the reaction mixture. In one embodiment, an olefin metathesis catalyst may be generated in situ as described herein and subsequently utilized in an metathesis reaction, wherein the nitrogen-containing ligand(s) of the catalyst precursor may be selected such that the released nitrogen-containing ligand(s) do not contain carbon-carbon double bonds which may react with the generated olefin metathesis catalyst.

The oxygen-containing ligand may be a heteroaryl or heteroalkyl group comprising at least one oxygen ring atom. In some cases, the oxygen-containing ligand may be a bidentate ligand (e.g., a diolate), as described herein. In some cases, the oxygen-containing ligand may be a chiral ligand. In some embodiments, the oxygen-containing ligand may be attached to a surface of a solid support material, such as an inorganic substrate, polymer resin, or other solid support, via a covalent or a non-covalent bond (e.g., an ionic bond, a hydrogen bond, a dative bond, Van der Waals interactions, or the like). Thus, replacement of the nitrogen containing ligand(s) with the solid-supported oxygen-containing ligand(s) may generate a heterogeneous catalyst. For example, a silicon substrate may comprise —SiOH groups covalently bound to the surface of the substrate, wherein the —SiOH groups may coordinate the metal center of the catalyst precursor to form a heterogeneous, surface-bound catalyst.

Methods of the invention may be advantageous in that, in some cases, a catalyst may be prepared under relatively mild conditions and in high yields. For example, the replacement of the nitrogen-containing ligand(s) with oxygen-containing ligand(s) to form the catalyst may occur at a temperature of less than 100° C. and with a yield of at least 50%. In some cases, the replacement may occur with a yield of at least 50%, at least 60%, at least 70%, at least 80%, at least 90%, or, in some cases, at least 95%. In some embodiments, the replacement may occur at a temperature of less than 80° C., less than 60° C., less than 40° C., or, in some cases, less than 25° C. For example, the replacement of the nitrogen-containing ligand(s) with oxygen-containing ligand(s) may occur at room temperature. In some cases, the catalyst may be prepared by a relatively rapid reaction, with conversion of the catalyst precursor to the catalyst often occurring within 60 minutes or less, 30 minutes or less, or, in some cases, 15 minutes or less.

In some embodiments, the resulting catalyst may have the structure,

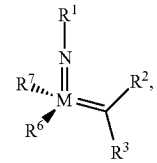

wherein M is Mo or W; R$^1$ is alkyl, heteroalkyl, aryl, or heteroaryl, optionally substituted; R$^2$ and R$^3$ can be the same or different and are hydrogen, alkyl, heteroalkyl, aryl, or heteroaryl, optionally substituted; $R^6$ and $R^7$ can be the same or different and are heteroalkyl or heteroaryl, optionally substituted, or $R^6$ and $R^7$ are joined together to form a bidentate ligand with respect to M, optionally substituted; and wherein $R^6$ and $R^7$ each comprise at least one oxygen atom.

In some cases, $R^6$ and $R^7$ may be joined together to form a chiral, bidentate ligand of at least 80% optical purity and having sufficient rigidity such that a reaction site is of sufficient shape specificity, defined in part by the chiral, bidentate ligand and a $M=N-R^1$ site, to cause a molecular substrate having a plane of symmetry to react with a M=C center at the reaction site, forming a product that has at least a 50% enantiomeric excess of at least one enantiomer present in the mixture, the product being free of a plane of symmetry. In some embodiments, the chiral, bidentate ligand may comprise two linked oxygen atoms such that a group of atoms defining the shortest chemical bond pathway between the two oxygen atoms has at least four atoms. Examples of chiral bidentate ligands include biphenolates and binaphtholates, optionally substituted with alkyl, alkenyl, alkynyl, cycloalkyl, cycloalkenyl, cycloalkynyl, aryl, alkaryl, aralkyl, optionally interrupted or terminated by heteroatoms, carbonyl groups, cyano, $NO_2$, alkoxy, aryloxy, hydroxy, amino, thioalkyl, thioaryl, sulfur-containing groups, halides, substituted derivatives thereof, and the like. In some cases, the chiral, bidentate ligand may be substituted at positions in proximity of the metal center to impart stereoselectivity to the reactive site of the catalyst.

In some cases, catalysts comprising one or more sterically large ligands may be synthesized. For example, at least one of $R^1$-$R^3$, $R^6$, and $R^7$ may contain sterically large groups, such as tert-butyl, isopropyl, phenyl, naphthyl, adamantyl, substituted derivatives thereof, and the like. Sterically large ligands may also include ligands comprising substituents positioned in close proximity to the metal center when the ligand is bound to the metal. Methods as described herein may be used to synthesize catalysts that may otherwise be difficult or impossible to prepare due to the presence of one or more sterically large groups bound to or proximate the metal center, i.e., steric "crowding" around the metal center. For example, catalysts described herein may comprise sterically large groups on the imido, alkoxide, and/or alkylidene ligands. In an illustrative embodiment, methods of the invention may be used to synthesize $Mo(N-2,6-Br_2-4-MeC_6H_2)(CHCMe_3)$[rac-Biphen], where Biphen is 3,3'-di-t-butyl-5,5',6,6'-tetramethyl-1,1'-biphenyl-2,2'-diolate.

Upon formation of the catalyst in a reaction vessel, a one-pot procedure may be performed, wherein the catalyst may be generated in situ and may be subsequently employed in a chemical reaction, in the same reaction vessel. Those of ordinary skill in the art would be able to select the appropriate catalyst in combination with the chemical reaction to be performed. The ability to, in a single reaction vessel, generate a catalyst in situ and utilize the catalyst in a reaction, may facilitate the ability to screen a large number of catalysts for a particular reaction. Also, additional purification may be eliminated, which may be useful in cases where the catalyst structure may be difficult to isolate. In some cases, the reaction may be a carbon-carbon bond forming reaction. In some cases, the reaction may be an olefin metathesis reaction, such as a ring-closing reaction, a ring-opening reaction, or a cross-metathesis reaction. The catalyst may be present at a concentration of less than 100 mM, less than 50 mM, or less than 10 mM.

The catalyst may be provided in the reaction mixture in a sub-stoichiometric amount (e.g., catalytic amount). In certain embodiments, that amount is in the range of 0.01 to 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than or equal to about 20 mol %, about 10 mol %, about 5 mol %, or about 1 mol % relative to the limiting reagent. In the case where the molecular formula of the catalyst complex includes more than one metal, the amount of the catalyst complex used in the reaction may be adjusted accordingly.

The products (e.g., catalysts, catalyst precursors) which may be produced by methods of the present invention may undergo further reaction(s) to afford desired derivatives thereof. Such permissible derivatization reactions can be carried out in accordance with conventional procedures known in the art. For example, potential derivatization reactions include metathesis reactions between the alkylidene moiety of the catalyst or catalyst precursor and an olefin, such that $R^2$ and $R^3$ are replaced.

As suitable, the catalysts employed in the present invention may involve the use of metals which can mediate a particular desired chemical reaction. In general, any transition metal (e.g., having d electrons) may be used to form the catalyst, e.g., a metal selected from one of Groups 3-12 of the periodic table or from the lanthanide series. However, in some embodiments, the metal may be selected from Groups 3-8, or, in some cases, from Groups 4-7. In some embodiments, the metal may be selected from Group 6. According to the conventions used herein, the term "Group 6" refers to the transition metal group comprising chromium, molybdenum, and tungsten. In some cases, the metal is molybdenum or tungsten. It may be expected that these catalysts will perform similarly because they are known to undergo similar reactions, such as metathesis reactions. However, the different ligands are thought to modify the catalyst performance by, for example, modifying reactivity and preventing undesirable side reactions. In a particular embodiment, the catalyst comprises molybdenum. Additionally, the present invention may also include the formation of heterogeneous catalysts containing forms of these elements.

As used herein, a "nitrogen-containing ligand" (e.g., $R^4$ and/or $R^5$) may be any species capable of binding a metal center via a nitrogen atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Mo or W metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. The nitrogen-containing ligand may be selected to interact with an oxygen-containing ligand such that the oxygen-containing ligand can readily replace the nitrogen-containing ligand to generate the catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In one embodiment, $R^4$ and $R^5$ may be pyrrolyl groups. In some embodiments, the nitrogen-containing ligand may be chiral and may be provided as a racemic mixture or a purified stereoisomer.

In some cases, $R^4$ and $R^5$ may be joined together to form a bidentate ligand which, when bound to the metal center, forms a metallacycle structure with the metal center. Bidentate ligands may be any species having at least two sites capable of binding a metal center. For example, the bidentate ligand may comprise at least two heteroatoms that coordinate the metal center, or a heteroatom and an anionic carbon atom that coordinate the metal center. Examples of bidentate ligands suitable for use in the invention include, but are not limited to, aryl and heteroaryl groups, linked directly or via alkyl, heteroalkyl, aryl, and/or heteroaryl groups, substituted derivatives thereof, and the like.

As used herein, the term "oxygen-containing ligand" may be used to refer to ligands comprising at least one oxygen atom capable of coordinating a metal atom (e.g., $R^6$ and/or $R^7$). The term "oxygen-containing ligands" may also describe ligand precursors comprising at least one hydroxyl group, wherein deprotonation of the hydroxyl group results in a negatively charged oxygen atom, which then coordinates a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center. The oxygen-containing ligand may also be a bidentate ligand, wherein the ligand coordinates the metal center via two oxygen atoms (e.g., "dialkoxide ligand").

The oxygen-containing ligand may also be attached to a surface of a solid support material, such as an inorganic substrate (e.g., $SiO_2$, alumina, etc.), polymer resin, or the like, via a covalent or a non-covalent bond. The solid support material may be any material capable of forming a bond with catalysts as described herein. In some cases, the solid support material may comprise functional groups (e.g., SiOH groups) positioned at the surface of the solid support material, wherein the functional groups may form a bond with the catalyst or catalyst precursor. The bond may be a covalent bond, an ionic bond, a hydrogen bond, a dative bond, or the like. The bond may also comprise Van der Waals interactions. The support material may be selected to have a particular surface area wherein the solid support material may contact a sufficient amount of a reagent (e.g., catalyst, catalyst precursor, other reagents, etc.) to allow interaction between the surface functional groups and the reagent. In some embodiments, the support material has a high surface area. In some cases, the support material has a surface area of at least 50 $mm^2$, at least 100 $mm^2$, at least 200 $mm^2$, at least 300 $mm^2$, at least 400 $mm^2$, or at least 500 $mm^2$.

In some cases, the oxygen-containing ligand may be chiral and may be provided as a racemic mixture or a purified stereoisomer. In some embodiments, the chiral, oxygen-containing ligand may be present in at least 80% optical purity, i.e., the oxygen-containing ligand sample contains 90% of one enantiomer and 10% of the other. In some embodiments, the chiral, oxygen-containing ligand may be at least 90% optically pure, at least 95% optically pure, or, in some cases, at least 99% optically pure.

In some cases, the catalyst may comprise a bidentate, oxygen-containing ligand (e.g., dialkoxide) having sufficient rigidity such that, in conjunction with an M=N—$R^1$ site, the combination of the bidentate, oxygen-containing ligand and the M=N—$R^1$ site in part may confer shape specificity to a reaction site where the catalyst reacts with a reactant such as, for example, an olefin. In some embodiments, the shape specificity, imparted by rigidity of the bidentate, oxygen-containing ligand, may be sufficient to allow a mixture of two enantiomeric reactants (e.g., olefins) to react with a M=C center of the reaction site at different rates. That is, the catalyst may be designed to have shape specificity sufficient to differentiate between enantiomers of a reactant by sterically interacting with one enantiomer almost exclusively or exclusively to achieve enantiomeric selectivity, that is, a preference for one enantiomer over the other. Enantiomeric selectivity by kinetic resolution involves reducing the steric interactions in the transition state of the reaction of the substrate at the catalyst such that the transition state involving one enantiomer is of lower energy than the transition state of the other enantiomer. Consequently, the term shape specificity in the present invention refers to the shape of an M=C reaction site in the transition state, as formed by the surrounding ligands, such that upon reaction of the substrate with the metal compound, one enantiomer "fits into" the binding site with less steric interaction than the other enantiomer. The transition state energy is lower for the enantiomer with a better "fit" or shape specificity over the other.

In another embodiment, the chiral bidentate, oxygen-containing ligand of at least 80% optical purity has sufficient rigidity such that a reaction site is of sufficient shape specificity, defined in part by the bidentate, oxygen-containing ligand and a M=N—$R^1$ site, to cause a molecular substrate having a plane of symmetry to react with a M=C center at the reaction site forming a catalytic olefin metathesis product that is free of a plane of symmetry. The product has at least a 50% enantiomeric excess of at least one enantiomer present in the mixture. In some cases, the product may have at least a 60%, 70%, 80%, or 90% enantiomeric excess of at least one enantiomer present in the mixture. A method to screen for bidentate, oxygen-containing ligands having sufficient rigidity for shape specificity purposes involves obtaining an enantiomeric mixture of a test bidentate, oxygen-containing ligand, isolating one enantiomer and measuring a specific rotation. A bidentate, oxygen-containing ligand of sufficient rigidity would provide a specific rotation as opposed to reverting back to an enantiomeric mixture.

Catalysts and catalyst precursors of the invention may comprise substituted imido groups (e.g., N—$R^1$). Without wishing to be bound by theory, the imido group may stabilize the organometallic compositions described herein by providing steric protection and/or reducing the potential for bimolecular decomposition. In some cases, $R^1$ may be selected to be sterically large or bulky, including phenyl groups, substituted phenyl groups (e.g., 2,6-disubstituted phenyls, 2,4,6-trusubstituted phenyls), polycyclic groups (e.g., adamantyl), or other sterically large groups. In some embodiments, $R^1$ may be 2,6-dialkylphenyl, such as 2,6-diisopropylphenyl. Catalysts and catalyst precursors of the invention may further comprise substituted alkylidene groups (e.g., $CR^2R^3$). The alkylidene groups may be mono-substituted (e.g., one of $R^2$ and $R^3$ is hydrogen) or di-substituted with, for example, alkyl, heteroalkyl, aryl, or heteroaryl groups, optionally substituted. In some cases, the alkylidene may be mono-substituted with, for example, t-butyl, dimethylphenyl, or the like.

The combination of imido, alkoxide, and/or alkylidene ligands may be selected to suit a particular application. For example, in some cases, sterically large or sterically bulky ligands and/or ligand substituents may impart a higher degree of stability to a catalyst, while, in some cases, lowering the reactivity of the catalyst. In some cases, smaller ligands and/or substituents may generate more reactive catalysts that may have decreased stability. Those of ordinary skill in the art would be able to balance such factors and select the appropriate combination of ligands for catalysts of the invention.

Solvents which may be used in methods of the invention include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like. In some embodiments, the solvent may be diethyl ether or dichloromethane.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s).

The term "organometallic" is given its ordinary meaning in the art and refers to compositions comprising at least one metal atom bound to one or more than one organic ligand.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "heteroalkyl" is given its ordinary meaning in the art and refers to alkyl groups as described herein in which one or more atoms is a heteroatom (e.g., oxygen, nitrogen, sulfur, and the like).

The term "aryl" is given its ordinary meaning in the art and refers to single-ring aromatic groups such as, for example, 5-, 6- and 7-membered single-ring aromatic groups. The term "heteroaryl" is given its ordinary meaning in the art and refers to aryl groups as described herein in which one or more atoms is a heteroatom (e.g., oxygen, nitrogen, sulfur, and the like). Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least on functional group that has sufficient ionic character to coordinate the metal center, such as a biphenolate group, for example.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be Modified by substitution, in this definition, to become, e.g., a cyclohexyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, lower arylalkyloxyalkyl, and the like.

EXAMPLES

Example 1

All complexes were handled using standard Schlenk techniques or in a Vacuum Atmospheres glove box under an argon or dinitrogen atmosphere. All solvents were dried, degassed, and stored over activated molecular sieves in a dinitrogen-filled glovebox. Pyrrole was distilled from $CaH_2$ in an inert atmosphere and lithium pyrrolide was prepared using published procedures. $Mo(N-2,6-i-Pr_2C_6H_3)(CHCMe_2Ph)(OTf)_2DME$, $Mo(NAd)(CHR)(OTf)_2(DME)$, and $Mo(N-2,6-Br_2-4-MeC_6H_2)(CHCMe_3)(OTf)_2(DME)$ were synthesized by published procedures. Elemental analyses were performed by Desert Analytics, Tucson, Ariz. Little or no competitive deprotonation of the alkylidene to give an alkylidyne complex was observed. The compounds were sensitive to air and moisture and Could be recrystallized readily from toluene or mixtures of pentane and ether.

Example 2

Synthesis of $Mo(N-2,6-i-Pr_2C_6H_3)(CHCMe_3)(NC_4H_4)_2$

The following procedure was used to prepare the title compound. To a −35° C. solution of 0.193 g (0.27 mmol) $Mo(NAr)(CHCMe_3)(OTf)_2(DME)$ in 4 mL diethyl ether was added 38.6 mg (0.53 mmol) of $LiNC_4H_4$ as a solid in one portion. The mixture was stirred at room temperature for 1 hour, then all volatiles were removed in vacuo. The resulting brown powder was extracted with 5 mL of toluene and the solution was filtered through celite. The celite was washed with toluene (1 mL) and the resulting solution was taken to dryness in vacuo. The product was recrystallized from mixtures of pentane/toluene or pure toluene at −35° C. as a toluene solvate. $^1$H NMR (300 MHz, toluene-d$_8$) δ 13.5 (br s, 1H, MoCHR), 7-6.2 (v br s, overlapping, 11H, Ar—H and NC$_4$H$_4$), 3.8-2.9 (br s, 2H, i-Pr), 1.3 (br s, 6H, CMe$_3$), 1.1 (br s, 12H, i-Pr).

Example 3

Synthesis of Mo(N-2,6-i-Pr$_2$C$_6$H$_3$)(CHCMe$_2$Ph)(NC$_4$H$_4$)$_2$

The following procedure was used to prepare the title compound. LiNC$_4$H$_4$ (410 mg, 5.62 mmol) was added as a solid in several small portions a −40° C. solution of 2.223 g (2.81 mmol) Mo(NAr)(CHCMe$_2$Ph)(OTf)$_2$(DME) in 60 mL of diethyl ether. The mixture was stirred at room temperature for 1 hour. All volatiles were removed in vacuo and the resulting powder was extracted with 65 mL of a 1:1 mixture of toluene and pentane and the solution was filtered through celite. The celite was washed with toluene (3×15 mL) and the resulting solution was reduced to dryness in vacuo. The solid was recrystallized from pentane −35° C.; yield 1.2 g (80%): $^1$H NMR (toluene-d$_8$, 500 MHz) (223 K) δ 13.55 (s, 1H, MoCHR), 13.16 (s, 1H, MoCHR), 7.4-6.7 (m, Ar—H, NC$_4$H$_4$), 5.85 (s, 1H, NC$_4$H$_4$), 5.10 (s, 1H, NC$_4$H$_4$), 4.91 (s, 1H, NC$_4$H$_4$), 4.83 (s, 1H, NC$_4$H$_4$), 3.85 (sept, 2H, i-Pr methine), 2.85 (sept, 2H, i-Pr methine), 1.75 (s, 6H, MoCHCMe$_2$Ph), 1.71 (s, 3H, MoCHCMe$_2$Ph), 1.68 (s, 3H, MoCHCMe$_2$Ph), 1.19 (br d, 12H, Ar-i-Pr), 1.12 (d, 3H, Ar-i-Pr), 1.03 (overlapping d, 6H, Ar-i-Pr), 0.55 (d, 3H, Ar-i-Pr); (323 K): δ 13.18 (s, 1H, MoCHR), 7.33 (d, 2H, MoCHCMe$_2$Ar), 7.18 (t, 2H, MoCHCMe$_2$Ar), 7.05 (t, 1H, MoCHCMe$_2$Ar), 6.86 (m, 3H, MoNAr), 6.44 (s, 4H, NC$_4$H$_4$), 6.14, (s, 4H, NC$_4$H$_4$), 3.22 (sept, 2H, i-Pr methine), 1.56 (s, 6H, MoCHCMe$_2$Ar), 0.96 (d, 12H, i-Pr methyl). $^{13}$C NMR (CD$_2$Cl$_2$, 126 MHz, 223 K): 313.9 (J$_{CH}$ 122.8 Hz), 293.9 (J$_{CH}$ 121.3 Hz). Analysis calcd. For C$_{30}$H$_{37}$MoN$_3$ (found): C, 67.28 (67.38), H, 6.96 (7.20), Mo 17.91, N, 7.85 (7.70).

Example 3

Synthesis of Mo(NAd)(CHCMe$_2$Ph)(NC$_4$H$_4$)$_2$

The following procedure was used to prepare the title compound. LiNC$_4$H$_4$ (169 mg, 2.32 mmol) was added as a solid in small portions to a −35° C. solution of 0.890 g (1.16 mmol) Mo(NAd)(CHCMe$_2$Ph)(OTf)$_2$(DME) in 50 mL of diethyl ether. The mixture was stirred at room temperature for 1.5 h, then all volatiles were removed in vacuo. The resulting brown powder was extracted with toluene and the solution was filtered through celite. The celite was washed with toluene and the combined filtrates were taken to dryness in vacuo. The off-white solid may be recrystallized from toluene at −35° C.; yield 420 mg (2 crops, 71%): $^1$H NMR (C$_6$D$_6$, 500 MHz, 293 K) δ 13.6 (br s, 1H, MoCHR), 12.8 (br s, 1H, MoCHR), 7.5, (br s, 4H, MoCHCMe$_2$Ph), 7.0-4.7 (2 overlapping br s, MoCHCMe$_2$Ph and NC$_4$H$_4$), 1.8-1.6 (br multiplet, 15H, MoNAd), 1.3 (br s, 6H, MoCHCMe$_2$Ph). $^{13}$C (CD$_2$Cl$_2$ 126 MHz, 223K): 316.1 (J$_{CH}$ 118.2 Hz), 295.5 (J$_{CH}$ 111.3 Hz).

Analysis calcd. For C$_{28}$H$_{35}$MoN$_3$ (found): C, 66.00 (65.10), H, 6.92 (6.60), Mo 18.83, N, 8.25 (7.04).

Example 4

Synthesis of Mo(N-2,6-Br$_2$-4-MeC$_6$H$_2$)(CHCMe$_3$)(NC$_4$H$_4$)$_2$

The following procedure was used to prepare the title compound. LiNC$_4$H$_4$ (35.4 mg, 0.485 mmol) in diethyl ether (~2 mL) was added to a −40° C. solution of 0.198 g (0.243 mmol) Mo(NAr)(CHCMe$_3$)(OTf)$_2$(DME) in 3 mL of dichloromethane. The mixture was stirred at room temperature for 1 hour and all volatiles were removed in vacuo. The resulting red-brown powder was extracted with benzene and the solution was filtered through celite. The celite was washed with benzene and the combined filtrates were taken to dryness in vacuo. The product was recrystallized from pentane containing a few drops of benzene at −35° C.; yield 94 mg (62%): $^1$H NMR (300 MHz, C$_6$D$_6$, 293 K) δ 13.4 (br s, 1H MoCHR), 6.8-6.4 (br overlapping s, 10H, MoNAr and NC$_4$H$_4$), 3.1 (s, 3H, MoNAr methyl), 1.4 (br s, 9H, MoCHCMe$_3$). Analysis calcd. For C$_{20}$H$_{23}$MoBr$_2$N$_3$ (found): C, 42.81 (42.52), H, 4.13 (4.12), Mo 17.10, Br 28.48, N, 7.49 (6.83).

Example 5

Synthesis of Mo(NAd)(CHCMe$_2$Ph)(NC$_4$H$_4$)$_2$(PMe$_3$)

The following procedure was used to prepare the title compound. Excess trimethylphosphine (50 μL) was added to 150 mg of Mo(NAd)(CHCMe$_2$Ph)(NC$_4$H$_4$)$_2$ in diethyl ether. The mixture was stirred at room temperature for 30 minutes and the solvent was removed in vacuo. Mo(NAd)(CHCMe$_2$Ph)(NC$_4$H$_4$)$_2$(PMe$_3$) was crystallized from pentane as orange blocks; yield 100 mg (58%): NMR ($^1$H, 300 MHz, C$_6$D$_6$) δ 12.49 (d, 1H, 4.8 Hz, CHCMe$_2$Ph), 8.41 (m, 2H, Ar), 7.05 (m, 6H, Ar), 6.80 (s, 4H, NC$_4$H$_4$), 6.40 (s, 4H, NC$_4$H$_4$), 2.43 (s, 6H), 1.82 (s, 6H), 1.73 (s, 3H, Ad), 1.35 (s, 6H), 0.46 (d, 9H, J$_{HP}$ 9.2 Hz, PMe$_3$); $^{13}$C NMR (C$_6$D$_6$) δ 301.73 (d, MoCHCMe$_2$Ph, $^2$J$_{C-P}$ 19.5 Hz), 148, 132.19, 129.13, 126.37, 125.96, 109.16, 108.62, 42.22, 36.21, 30.03, 16.50 (d, PMe$_3$, J$_{C-P}$ 25 Hz). Analysis calcd. For C$_{31}$H$_{44}$MoN$_3$P (found): C, 63.58 (63.37), H, 7.57 (7.45), Mo 16.38, N, 7.18 (6.04), P 5.29.

Example 6

The reactivity of {Mo(NR)(CHCMe$_2$R')(NC$_4$H$_4$)$_2$}$_2$ species towards a Lewis acid (e.g., B(C$_6$F$_5$)$_3$) and a Lewis base (e.g., PMe$_3$) was observed by NMR.

Figure 3:
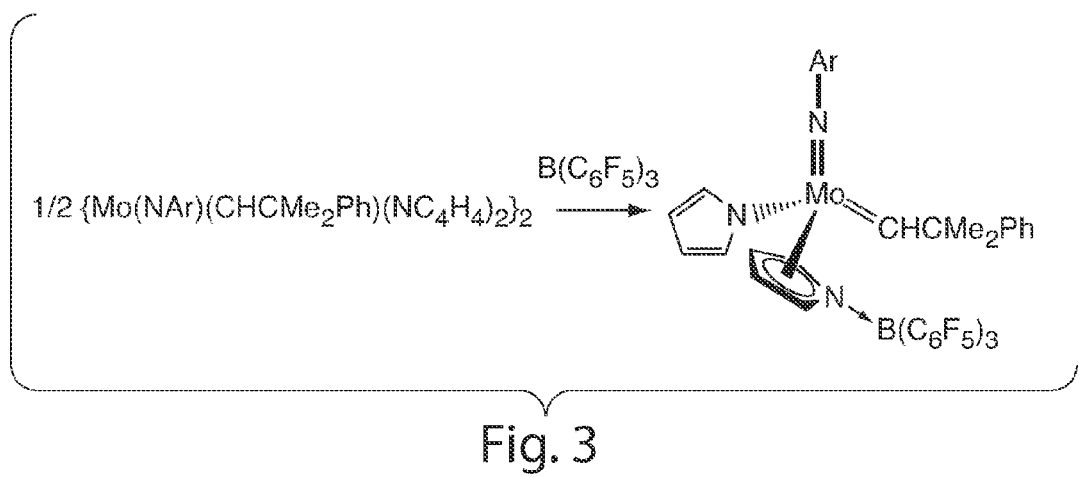
FIG. 3 shows the reaction of a Lewis acid with a composition of the invention.

For example, Mo(N-2,6-i-Pr$_2$C$_6$H$_3$)(CHCMe$_2$Ph)(η$^1$-NC$_4$H$_4$)(η$^5$-C$_4$H$_4$NB(C$_6$F$_5$)$_3$) was synthesized according to the following procedure. To 23.0 mg (0.021 mmol) of {Mo(N-2,6-i-Pr$_2$C$_6$H$_3$)(CHCMe$_2$Ph)(NC$_4$H$_4$)$_2$}$_2$ in ~0.25 mL of C$_6$D$_6$ was added B(C$_6$F$_5$)$_3$ (22 mg, 0.043 mmol) in ca. 0.25 mL C$_6$D$_6$. The solution was transferred to a Teflon-sealed NMR tube and the $^1$H NMR spectrum was recorded. The Lewis acid B(C$_6$F$_5$)$_3$ was observed to react immediately with {Mo(NAr)(CHCMe$_2$Ph)(NC$_4$H$_4$)$_2$}$_2$ to yield a proposed mixture of syn and anti alkylidenes of the adduct shown in FIG. 3. The four η$^5$-pyrrolyl protons in the major (syn) isomer were found at 7.7, 7.2, 5.7, and 5.4 ppm in benzene-d$_6$. $^1$H NMR (500 MHz, 293 K) δ 13.89 (s, 1H, MoCHR minor isomer), 13.08 (s, 1H, MoCHR major isomer), 7.72 (br s, 1H, η$^5$-C$_4$H$_4$NB(C$_6$F$_5$)$_3$), 7.28 (br s, 1H, η$^5$-C$_4$H$_4$NB(C$_6$F$_5$)$_3$), 7.08 (m, 4H, MoCHCMe$_2$Ph), 7.02 (d, J$_{HH}$7.6 Hz, 2H, η$^1$-NC$_4$H$_4$), 6.87 (m, 1H, MoCHCMe$_2$Ph), 6.78 (d, J$_{HH}$7.6 Hz, 2H, η$^1$-NC$_4$H$_4$), 5.78 (br s, 1H, η$^5$-C$_4$H$_4$NB(C$_6$F$_5$)$_3$), 5.41, (br s, 1H, η$^5$-C$_4$H$_4$NB(C$_6$F$_5$)$_3$), 2.82 (br s, 2H, i-Pr methine), 1.51 (s, 3H, MoCHCMe$_2$Ph), 1.25 (s, 3H, MoCHCMe$_2$Ph), 0.92 (br mult, 12H, i-Pr methyls).

Addition of one equivalent of PMe$_3$ to Mo(NAd)(CHCMe$_2$Ph)(NC$_4$H$_4$)$_2$ using a similar procedure resulted in immediate formation of syn-Mo(NAd)(CHCMe$_2$Ph)(η$^1$-NC$_4$H$_4$)$_2$(PMe$_3$), wherein the alkylidene proton resonance was observed at 12.49 ppm with J$_{HP}$=5 Hz. An X-ray structural study showed that trimethylphosphine was bound to one of the CN$_{imido}$N$_{pyrrolyl}$ faces of the pseudotetrahedral species, which is the face analogous to the CNO face where trimethylphosphine is observed to bind in bisalkoxide species.

Example 7

Figure 5:
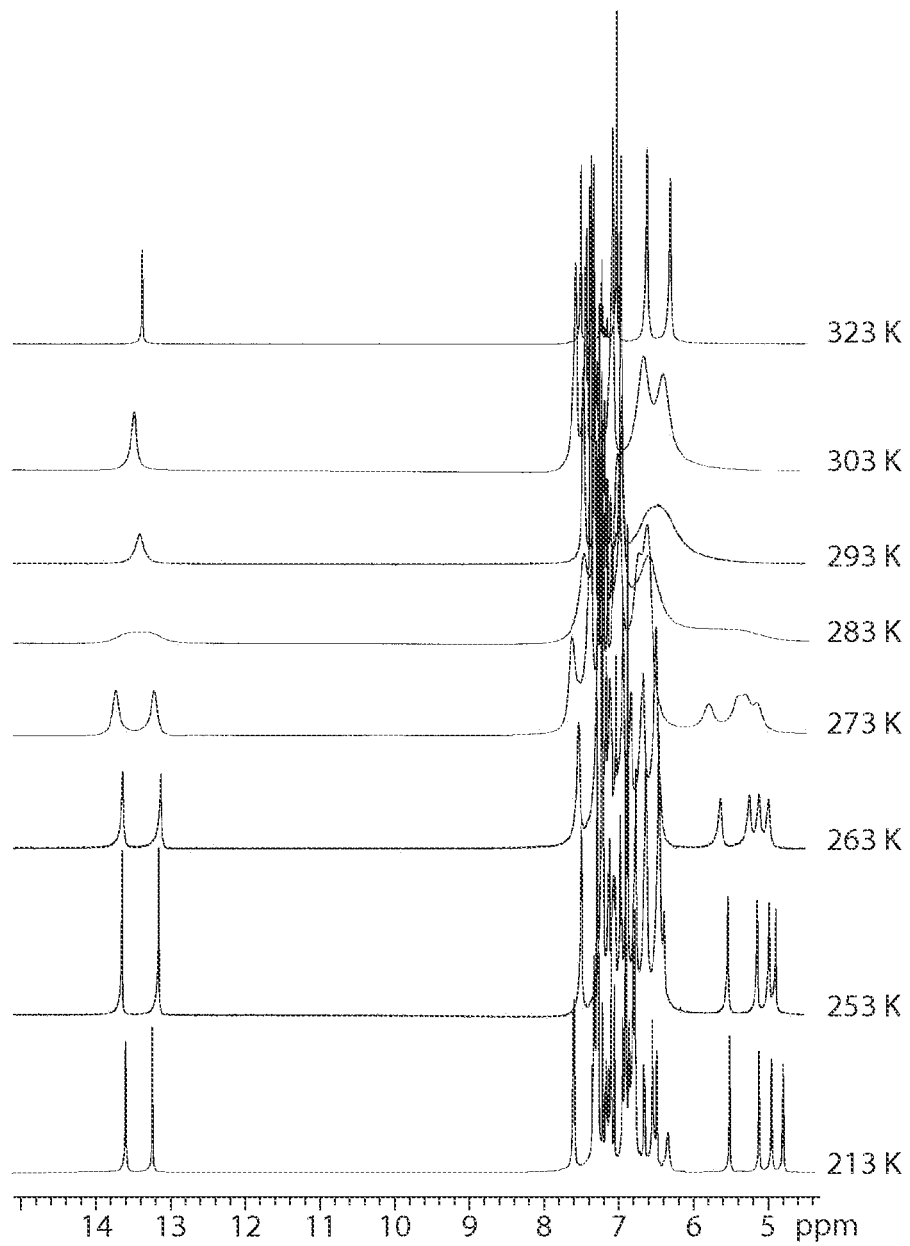
FIG. 5 shows the variable temperature NMR spectra of Mo(NAr)(CHCMe$_2$Ph)(NC$_4$H$_4$)$_2$ in toluene-d$_8$.

The NMR spectra of the catalyst precursor complexes were then studied. The dipyrrolyl complexes were observed to be fluxional on the proton NMR time scale. At 22° C., the spectra contained broad resonances, for example, for Mo(NAr)(CHCMe$_2$Ph)(NC$_4$H$_4$)$_2$ in toluene-d$_8$ (at 500 MHz), as shown in FIG. 5. At high temperature, one alkylidene resonance at ~13.3 ppm and two pyrrolyl resonances at ~6.1 and ~6.3 ppm were observed. At low temperatures two alkylidene resonances at ~43.2 and ~13.6 ppm were observed in a 1:1 ratio and the pyrrolyl proton resonances were resolved into an obscured set of resonances downfield of 6.3 ppm, along with a pattern of four sharp resonances near 5 ppm. No fluoride resonance were observed in the $^{19}$F NMR spectrum, and no solvent resonances were observed in the $^1$H NMR spectrum upon addition of trimethylphosphine, which yielded a base adduct. A $^{13}$C NMR. spectrum of Mo(NAr)(CHCMe$_2$Ph)(NC$_4$H$_4$)$_2$ at −50° C. in methylene chloride-d$_2$ revealed resonances at 313.9 ppm (J$_{CH}$=122.8 Hz) and 293.9 ppm (J$_{CH}$=121.3 Hz), characteristic of syn alkylidene species.

The NMR spectra at high-temperatures were consistent with a C$_s$ symmetric Mo(NR)(CHCMe$_2$R')(ζ$^1$-NC$_4$H$_4$)$_2$ species on the NMR time scale in which the pyrrolyl ligands were η$^1$ on average and rotated rapidly about the Mo—N bonds. Variable temperature spectra were identical at different concentrations, indicating that a small fraction of the dimer had dissociated into monomers in which interconversion of η$^1$-NC$_4$H$_4$ and η$^5$-NC$_4$H$_4$ ligands was facile.

Example 8

The reactivity of {Mo(NR)(CHCMe$_2$R')(NC$_4$H$_4$)$_2$}$_2$ species towards alcohols was observed. The molybdenum catalyst precursor (ca. 0.02 mmol) was dissolved in 0.2 mL of C$_6$D$_6$, and an equimolar amount of diol or, alternatively, two equivalents of alcohol in 0.3 mL of C$_6$D$_6$, were combined in a Teflon-sealed NMR tube. The $^1$H NMR spectrum was recorded within 15 minutes. All diols and alcohols examined proceeded to completion by the time the $^1$H NMR spectrum was recorded.

Addition of two equivalents of monoalcohols (e.g., Me$_3$COH or (CF$_3$)$_2$MeCOH) or one equivalent of a biphenol or binaphthol to ~10 mM solutions of the Mo(NR)(CHCMe$_2$R')(NC$_4$H$_4$)$_2$ (NR=NM or NAr) species resulted in rapid formation of two equivalents of pyrrole and the corresponding bisalkoxide or diolate complexes. The reaction was rapid and proceeded in ~100% yield in all combinations screened, including the sterically-challenging combination of 2,6-diisopropylphenylimido precursor reacting with H$_2$[Biphen] (H$_2$[Biphen]=3,3'-Di-t-butyl-5,5',6,6'-tetramethyl-1,1'-Biphenyl-2,2'-diol). In the case of 3,3'-bis(2,4,6-triisopropylphenyl)-2,2'-binaphthol, the resulting binaphtholate appeared to bind one equivalent of pyrrole weakly, but the corresponding THF adduct was generated immediately upon addition of one or more equivalents of THF. In some cases, catalysts that have been isolated only as THF adducts, or that have proven to be too unstable to isolate, may be prepared from dipyrrolyl complexes.

Example 9

Synthesis and Catalytic Activity of Mo(N-2,6-Br$_2$-4-MeC$_6$H$_2$)(CHCMe$_3$)[rac-Biphen]

Mo(N-2,6-Br$_2$-4-MeC$_6$H$_2$)(CHCMe$_3$)[Biphen] was prepared according to methods as described herein and was subsequently evaluated for its catalytic activity. Previous attempts to prepare this species through addition of K$_2$[Biphen] to Mo(N-2,6-Br$_2$-4-MeC$_6$H$_2$)(CHCMe$_3$)(OTf)$_2$(DME) did not produce the desired species in pure form and/or in a practical yield. However, using the methods described herein, Mo(N-2,6-Br$_2$-4-MeC$_6$H$_2$)(CHCMe$_3$)(NC$_4$H$_4$)$_2$ reacted with rac-H$_2$[Biphen] in benzene rapidly to yield the Mo(N-2,6-Br$_2$-4-MeC$_6$H$_2$)(CHCMe$_3$)[rac-Biphen] species in high yield. The alkylidene proton in Mo(N-2,6-Br$_2$-4-MeC$_6$H$_2$)(CHCMe$_3$)[rac-Biphen] was found at 11.3 ppm with a J$_{CH}$ coupling constant of 132.6 Hz, consistent with a syn alkylidene isomer. The catalytic activity of in situ prepared Mo(N-2,6-Br$_2$-4-MeC$_6$H$_2$)(CHCMe$_3$)[rac-Biphen] was confirmed through the ring-closing metathesis of ~80 equivalents of diallyl ether to dihydrofuran in 15 minutes at room temperature in C$_6$D$_6$.

The high reactivity of the {Mo(NR)(CHCMe$_2$R')(NC$_4$H$_4$)$_2$}$_2$ species towards alcohols and/or a Lewis acid or base (Example 6) further supported the concept that a small fraction of the dimer had dissociated into monomers in which interconversion of η$^1$-NC$_4$H$_4$ and η$^5$-NC$_4$H$_4$ ligands was facile.

Example 10

Crystals of the complexes were obtained and studied by X-ray diffraction. Low temperature diffraction data were collected on a Siemens Platform three-circle diffractometer coupled to a Bruker-AXS SMART Apex CCD detector with graphite-monochromated MoKα radiation (λ=0.71073 Å), performing φ and ω-scans. The structures were solved by direct methods using SHELXS and refined against F$^2$ on all data by full-matrix least squares with SHELXL-97. All non-hydrogen atoms were refined anisotropically. All hydrogen atoms were included into the model at geometrically calculated positions and refined using a riding model. The isotropic displacement parameters of all hydrogen atoms were fixed to 1.2 times the U value of the atoms they are linked to (1.5 times for methyl groups). Crystal and structural refinement data for the structure is listed below.

Figure 4:
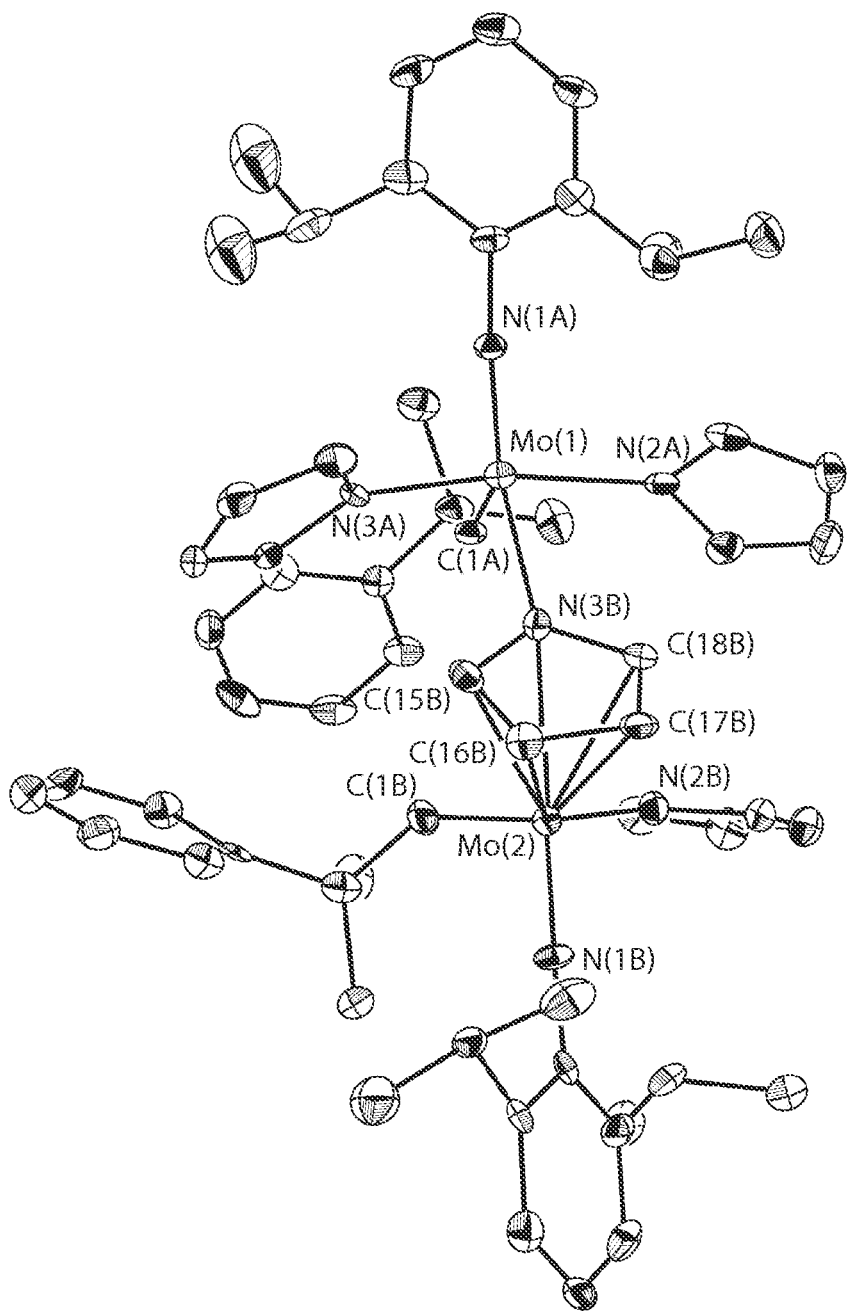
FIG. 4 shows the thermal ellipsoid plot (50% probability level) of the structure of the dimer, {Mo(NAr)(syn-CHCMe$_2$Ph)($\eta^5$-NC$_4$H$_4$)($\eta^1$-NC$_4$H$_4$)}{Mo(NAr)(syn-CHCMe$_2$Ph)($\eta^1$-NC$_4$H$_4$)$_2$}.

Crystals of {Mo(NAr)(syn-CHCMe$_2$Ph)(η$^5$-NC$_4$H$_4$)(η$^1$-NC$_4$H$_4$)}{Mo(NAr)(syn-CHCMe$_2$Ph)(η$^1$-NC$_4$H$_4$)$_2$} (Identification Code: 06172) grown at −40° C. from a mixture of pentane and toluene were coated with Paratone-N oil (an Exxon-Mobile™ product) in a dinitrogen-filled glovebox and examined under a microscope. A suitable crystal measuring 0.10×0.08×0.03 mm$^3$ was selected and mounted in a nylon loop. Initial examination of the data indicated that the space group was P2$_1$/c. However, no reasonable solution could be obtained via direct methods or from the Patterson map. The program CELL_NOW was used to re-determine the unit cell from 999 reflections sampled from several regions in the hemisphere of data. The resulting, slightly different, unit cell was used to integrate the data in the SAINT software package in the triclinic setting. A solution in the space group P1 (#1) was refined isotropically and the routines ADDSYM and NEWSYM in Platon were used to confirm that the correct space group was indeed P2$_1$/c. Re-integration in the primitive, monoclinic setting followed by absorption correction with the SADABS package yielded the data set from which the correct initial solution was obtained. Confirmation of the space group/setting was substantiated by the successful refinement of the structure and use of the ADDSYM and NEWSYM functions in the Platon software package. FIG. 4 shows the thermal ellipsoid plot (50% probability level) of the structure of the dimer, {Mo(NAr)(syn-CHCMe$_2$Ph)($\eta^5$-NC$_4$H$_4$)($\eta^1$-NC$_4$H$_4$)}{Mo(NAr)(syn-CHCMe$_2$Ph)($\eta^1$-NC$_4$H$_4$)$_2$}.

The X-ray structural studies of Mo(N-2,6-i-Pr$_2$C$_6$H$_3$)(CHCMe$_2$Ph)(NC$_4$H$_4$)$_2$ showed that the compound existed as an unsymmetric dimer, {Mo(NAr)(syn-CHCMe$_2$Ph)($\eta^5$-NC$_4$H$_4$)($\eta^1$-NC$_4$H$_4$)}{Mo(NAr)(syn-CHCMe$_2$Ph)($\eta^1$-NC$_4$H$_4$)$_2$}, in which the nitrogen in the $\eta^5$-pyrrolyl behaves as a donor to the other Mo (FIG. 4). The electron count in the Mo(NAr)(syn-CHCMe$_2$Ph)($\eta^5$-NC$_4$H$_4$)($\eta^1$-NC$_4$H$_4$) half was 18, and in the Mo(NAr)(syn-CHCMe$_2$Ph)($\eta^1$-NC$_4$H$_4$)$_2$ (donor) half was 16. The Mo(NAr)(syn-CHCMe$_2$Ph)($\eta^1$-NC$_4$H$_4$)$_2$(donor) fragment was approximately a square pyramid with the alkylidene in the apical position. Bond distances and angles were listed in Table 1 and Table 2, respectively. The dimeric structure was consistent with the NMR spectra at low temperature, i.e., one half (containing Mo(2)) has no symmetry, while the second (containing Mo(1)) effectively has C$_s$ symmetric. (FIG. 5) The four sharp resonances near 5 ppm were assigned to the four protons in the $\eta^5$-NC$_4$H$_4$ that is bound to a chiral metal center.

Table 3 shows the X-ray crystal data and structure refinement for {Mo(NAr)(CHR)(NC$_4$H$_4$)$_2$}$_2$. Table 4 shows the atomic coordinates ($\times 10^4$) and equivalent isotropic displacement parameters (Å$^2 \times 10^3$) for {Mo(NAr)(CHR)(NC$_4$H$_4$)$_2$}$_2$, where U(eq) is defined as one third of the trace of the orthogonalized U$^{ij}$ tensor. Table 5 shows the bond lengths [Å] and angles [°] for {Mo(NAr)(CHR)(NC$_4$H$_4$)$_2$}$_2$. Table 6 shows the anisotropic displacement parameters (Å$^2 \times 10^3$) for {Mo(NAr)(CHR)(NC$_4$H$_4$)$_2$}$_2$. The anisotropic displacement factor exponent takes the form:

$$-2\pi^2[h^2 a^{*2} U^{11} + \ldots + 2hka^*b^* U^{12}].$$

Table 7 shows the hydrogen coordinates ($\times 10^4$) and isotropic displacement parameters (Å$^2 \times 10^3$) for {Mo(NAr)(CHR)(NC$_4$H$_4$)$_2$}$_2$.

TABLE 1

Selected bond distances for {Mo(NAr)(CHR)(NC$_4$H$_4$)$_2$}$_2$.

| Bond | Bond distance (Å) |
|---|---|
| Mo(1)—C(1A) | 1.859(5) |
| Mo(2)—C(1B) | 1.912(5) |
| Mo(1)—N(2A) | 2.082(4) |
| Mo—N(3A) | 2.097(4) |
| Mo(2)—N(2B) | 2.060(4) |
| Mo(2)—N(3B) | 2.479(4) |
| Mo(1)—N(3B) | 2.395(4) |
| Mo(2)-pyrrolyl centroid | 2.48 |
| Mo(2)—N(2B) | 2.060(4) |
| Mo(1)—Mo(2) | 4.53 |

TABLE 2

Selected bond angles for {Mo(NAr)(CHR)(NC$_4$H$_4$)$_2$}$_2$.

| Bonds | Bond angles (°) |
|---|---|
| N(1A)—Mo(1)—C(1A) | 99.5(2) |
| N(1A)—Mo(1)—N(3B) | 155.16(16) |
| N(2A)—Mo(1)—N(3A) | 150.98(16) |
| pyrrolyl centroid-Mo(2)—N(1B) | 157.3 |
| N(1B)—Mo(2)—C(1B) | 100.5(2) |
| N(1B)—Mo(2)—N(2B) | 101.80(17) |

TABLE 3

Crystal data and structure refinement for {Mo(NAr)(CHR)(NC$_4$H$_4$)$_2$}$_2$.

| | |
|---|---|
| Identification code | 06172 |
| Empirical formula | C$_{67}$H$_{82}$Mo$_2$N$_6$ |
| Formula weight | 1163.27 |
| Temperature | 100(2) K |
| Wavelength | 0.71073 Å |
| Crystal system | Monoclinic |
| Space group | P2$_1$/c |
| Unit cell dimensions | a = 24.903(12) Å   α = 90° |
| | b = 12.723(5) Å    β = 106.001(12)° |
| | c = 19.434(9) Å    γ = 90° |
| Volume | 5919(4) Å$^3$ |
| Z | 4 |
| Density (calculated) | 1.305 Mg/m$^3$ |
| Absorption coefficient | 0.469 mm$^{-1}$ |
| F(000) | 2440 |
| Crystal size | 0.10 × 0.08 × 0.03 mm$^3$ |
| Theta range for data collection | 1.70 to 21.97°. |
| Index ranges | −26 <= h <= 25, 0 <= k <= 13, 0 <= l <= 20 |
| Reflections collected | 7216 |
| Independent reflections | 7216 [R(int) = 0.1879] |
| Completeness to theta = 21.97° | 99.6% |
| Absorption correction | Empirical |
| Max. and min. transmission | 0.9861 and 0.9546 |
| Refinement method | Full-matrix least-squares on F$^2$ |
| Data/restraints/parameters | 7216/0/670 |
| Goodness-of-fit on F$^2$ | 1.013 |
| Final R indices [I>2sigma(I)] | R1 = 0.0412, wR2 = 0.0775 |
| R indices (all data) | R1 = 0.0753, wR2 = 0.0901 |
| Largest diff. peak and hole | 0.590 and −0.534 e.Å$^{-3}$ |

TABLE 4

Atomic coordinates ($\times 10^4$) and equivalent isotropic displacement parameters (Å$^2 \times 10^3$) for {Mo(NAr)(CHR)(NC$_4$H$_4$)$_2$}$_2$. U(eq) is defined as one third of the trace of the orthogonalized U$^{ij}$ tensor.

| | x | y | z | U(eq) |
|---|---|---|---|---|
| Mo(1) | 3042(1) | 8833(1) | 4794(1) | 15(1) |
| Mo(2) | 1260(1) | 9284(1) | 3435(1) | 16(1) |
| N(1A) | 3711(2) | 8566(3) | 5307(2) | 15(1) |
| N(2A) | 2949(2) | 7481(3) | 4169(2) | 18(1) |
| N(3A) | 2778(2) | 9826(3) | 5499(2) | 16(1) |
| N(1B) | 573(2) | 9542(3) | 2975(2) | 16(1) |
| N(2B) | 1584(2) | 8780(3) | 2624(2) | 18(1) |
| N(3B) | 2048(2) | 8621(3) | 4418(2) | 17(1) |
| C(1A) | 3201(2) | 9782(4) | 4150(3) | 17(1) |
| C(2A) | 3661(2) | 10288(4) | 3889(3) | 21(1) |
| C(3A) | 3722(2) | 9622(3) | 3256(3) | 29(2) |
| C(4A) | 4217(2) | 10277(4) | 4472(3) | 26(1) |
| C(5A) | 3493(2) | 11426(4) | 3668(3) | 17(1) |
| C(6A) | 3495(2) | 12174(4) | 4195(3) | 23(1) |
| C(7A) | 3377(2) | 13223(4) | 4019(3) | 26(1) |
| C(8A) | 3246(2) | 13539(4) | 3313(3) | 28(2) |
| C(9A) | 3221(2) | 12800(4) | 2784(3) | 26(1) |
| C(10A) | 3351(2) | 11751(4) | 2960(3) | 24(1) |
| C(11A) | 2805(2) | 7348(4) | 3437(3) | 21(1) |
| C(12A) | 2658(2) | 6321(4) | 3270(3) | 25(1) |

TABLE 4-continued

Atomic coordinates (×10⁴) and equivalent isotropic displacement parameters ($Å^2 \times 10^3$) for {Mo(NAr)(CHR)(NC$_4$H$_4$)$_2$}$_2$. U(eq) is defined as one third of the trace of the orthogonalized $U^{ij}$ tensor.

| | x | y | z | U(eq) |
|---|---|---|---|---|
| C(13A) | 2708(2) | 5785(4) | 3908(3) | 25(1) |
| C(14A) | 2886(2) | 6507(4) | 4449(3) | 22(1) |
| C(15A) | 2631(2) | 10869(4) | 5439(3) | 17(1) |
| C(16A) | 2388(2) | 11154(4) | 5966(3) | 21(1) |
| C(17A) | 2380(2) | 10237(4) | 6378(3) | 23(1) |
| C(18A) | 2621(2) | 9459(4) | 6080(3) | 21(1) |
| C(19A) | 4235(2) | 8243(4) | 5738(3) | 16(1) |
| C(20A) | 4556(2) | 7535(4) | 5453(3) | 22(1) |
| C(21A) | 5056(2) | 7183(4) | 5908(3) | 25(1) |
| C(22A) | 5231(2) | 7515(4) | 6605(3) | 29(2) |
| C(23A) | 4922(2) | 8235(4) | 6870(3) | 29(1) |
| C(24A) | 4421(2) | 8623(4) | 6443(3) | 23(1) |
| C(25A) | 4377(2) | 7171(4) | 4677(3) | 24(1) |
| C(26A) | 4814(2) | 7493(4) | 4293(3) | 31(2) |
| C(27A) | 4279(2) | 5983(4) | 4617(3) | 34(2) |
| C(28A) | 4093(2) | 9443(5) | 6726(3) | 33(2) |
| C(29A) | 4306(3) | 10534(5) | 6630(3) | 58(2) |
| C(30A) | 4091(3) | 9295(5) | 7494(3) | 58(2) |
| C(1B) | 1561(2) | 10676(4) | 3538(3) | 20(1) |
| C(2B) | 1398(2) | 11805(4) | 3341(3) | 21(1) |
| C(3B) | 1753(2) | 12191(4) | 2857(3) | 30(2) |
| C(4B) | 779(2) | 11925(4) | 2919(3) | 25(1) |
| C(5B) | 1506(2) | 12448(4) | 4032(3) | 18(1) |
| C(6B) | 1904(2) | 13232(4) | 4213(3) | 24(1) |
| C(7B) | 1966(2) | 13822(4) | 4826(3) | 29(1) |
| C(8B) | 1646(2) | 13645(4) | 5281(3) | 26(1) |
| C(9B) | 1259(2) | 12844(4) | 5127(3) | 26(1) |
| C(10B) | 1194(2) | 12252(4) | 4514(3) | 22(1) |
| C(11B) | 1845(2) | 9337(4) | 2197(3) | 24(1) |
| C(12B) | 1867(2) | 8742(4) | 1624(3) | 28(1) |
| C(13B) | 1622(2) | 7766(4) | 1694(3) | 26(1) |
| C(14B) | 1454(2) | 7811(4) | 2298(3) | 20(1) |
| C(15B) | 1666(2) | 9114(4) | 4704(3) | 20(1) |
| C(16B) | 1160(2) | 8570(4) | 4521(3) | 18(1) |
| C(17B) | 1234(2) | 7679(4) | 4127(3) | 18(1) |
| C(18B) | 1773(2) | 7743(4) | 4063(3) | 18(1) |
| C(19B) | 16(2) | 9695(4) | 2584(3) | 17(1) |
| C(20B) | −395(2) | 9841(4) | 2951(3) | 18(1) |
| C(21B) | −932(2) | 10069(4) | 2548(3) | 22(1) |
| C(22B) | −1069(2) | 10113(4) | 1815(3) | 22(1) |
| C(23B) | −669(2) | 9943(4) | 1458(3) | 26(1) |
| C(24B) | −115(2) | 9740(4) | 1835(3) | 18(1) |
| C(25B) | −252(2) | 9681(4) | 3752(3) | 22(1) |
| C(26B) | −623(2) | 10295(5) | 4123(3) | 38(2) |
| C(27B) | −281(2) | 8497(4) | 3899(3) | 29(2) |
| C(28B) | 320(2) | 9543(4) | 1433(3) | 22(1) |
| C(29B) | 362(2) | 10463(4) | 951(3) | 31(2) |
| C(30B) | 190(2) | 8524(4) | 995(3) | 26(1) |
| C(1T) | 6467(2) | 4402(4) | 3582(3) | 26(1) |
| C(2T) | 5918(2) | 4583(5) | 3559(3) | 31(2) |
| C(3T) | 5741(2) | 5558(5) | 3710(3) | 36(1) |
| C(4T) | 6107(3) | 6385(5) | 3884(3) | 33(2) |
| C(5T) | 6661(2) | 6216(5) | 3907(3) | 30(1) |
| C(6T) | 6837(2) | 5230(4) | 3765(3) | 25(1) |
| C(7T) | 6658(3) | 3336(4) | 3424(3) | 37(2) |

TABLE 5

Bond lengths [Å] and angles [°] for {Mo(NAr)(CHR)(NC$_4$H$_4$)$_2$}$_2$.

| | | | |
|---|---|---|---|
| Mo(1)—N(1A) | 1.725(4) | C(12A)—C(13A) | 1.391(7) |
| Mo(1)—C(1A) | 1.859(5) | C(13A)—C(14A) | 1.374(7) |
| Mo(1)—N(2A) | 2.082(4) | C(15A)—C(16A) | 1.374(7) |
| Mo(1)—N(3A) | 2.097(4) | C(16A)—C(17A) | 1.419(7) |
| Mo(1)—N(3B) | 2.395(4) | C(17A)—C(18A) | 1.366(7) |
| Mo(2)—N(1B) | 1.730(4) | C(19A)—C(24A) | 1.407(7) |
| Mo(2)—C(1B) | 1.912(5) | C(19A)—C(20A) | 1.414(7) |
| Mo(2)—N(2B) | 2.060(4) | C(20A)—C(21A) | 1.387(7) |
| Mo(2)—C(16B) | 2.373(5) | C(20A)—C(25A) | 1.523(7) |
| Mo(2)—C(15B) | 2.403(5) | C(21A)—C(22A) | 1.369(7) |
| Mo(2)—C(17B) | 2.456(5) | C(22A)—C(23A) | 1.384(7) |
| Mo(2)—C(18B) | 2.471(5) | C(23A)—C(24A) | 1.383(7) |
| Mo(2)—N(3B) | 2.479(4) | C(24A)—C(28A) | 1.518(7) |
| N(1A)—C(19A) | 1.404(6) | C(25A)—C(27A) | 1.531(7) |
| N(2A)—C(11A) | 1.379(6) | C(25A)—C(26A) | 1.535(7) |
| N(2A)—C(14A) | 1.379(6) | C(28A)—C(30A) | 1.507(8) |
| N(3A)—C(15A) | 1.373(6) | C(28A)—C(29A) | 1.516(8) |
| N(3A)—C(18A) | 1.375(6) | C(1B)—C(2B) | 1.513(7) |
| N(1B)—C(19B) | 1.400(6) | C(2B)—C(5B) | 1.532(7) |
| N(2B)—C(14B) | 1.383(6) | C(2B)—C(3B) | 1.537(7) |
| N(2B)—C(11B) | 1.383(6) | C(2B)—C(4B) | 1.542(7) |
| N(3B)—C(15B) | 1.376(6) | C(5B)—C(6B) | 1.382(7) |
| N(3B)—C(18B) | 1.390(6) | C(5B)—C(10B) | 1.394(7) |
| C(1A)—C(2A) | 1.519(7) | C(6B)—C(7B) | 1.380(7) |
| C(2A)—C(4A) | 1.530(7) | C(7B)—C(8B) | 1.362(7) |
| C(2A)—C(3A) | 1.534(7) | C(8B)—C(9B) | 1.378(7) |
| C(2A)—C(5A) | 1.536(7) | C(9B)—C(10B) | 1.381(7) |
| C(5A)—C(10A) | 1.386(7) | C(11B)—C(12B) | 1.359(7) |
| C(5A)—C(6A) | 1.396(7) | C(12B)—C(13B) | 1.407(7) |
| C(6A)—C(7A) | 1.389(7) | C(13B)—C(14B) | 1.352(7) |
| C(7A)—C(8A) | 1.379(7) | C(15B)—C(16B) | 1.395(7) |
| C(8A)—C(9A) | 1.382(7) | C(16B)—C(17B) | 1.409(7) |
| C(9A)—C(10A) | 1.394(7) | C(17B)—C(18B) | 1.383(7) |
| C(11A)—C(12A) | 1.371(7) | C(19B)—C(24B) | 1.403(7) |
| C(19B)—C(20B) | 1.411(7) | N(2B)—Mo(2)—C(15B) | 127.86(16) |
| C(20B)—C(21B) | 1.381(7) | C(16B)—Mo(2)—C(15B) | 33.95(16) |
| C(20B)—C(25B) | 1.513(7) | N(1B)—Mo(2)—C(17B) | 105.61(17) |
| C(21B)—C(22B) | 1.373(7) | C(1B)—Mo(2)—C(17B) | 141.38(19) |
| C(22B)—C(23B) | 1.378(7) | N(2B)—Mo(2)—C(17B) | 103.58(16) |

TABLE 5-continued

Bond lengths [Å] and angles [°] for {Mo(NAr)(CHR)(NC₄H₄)₂}₂.

| | | | |
|---|---|---|---|
| C(23B)—C(24B) | 1.395(7) | C(16B)—Mo(2)—C(17B) | 33.87(16) |
| C(24B)—C(28B) | 1.519(7) | C(15B)—Mo(2)—C(17B) | 55.28(17) |
| C(25B)—C(26B) | 1.532(7) | N(1B)—Mo(2)—C(18B) | 135.13(17) |
| C(25B)—C(27B) | 1.539(7) | C(1B)—Mo(2)—C(18B) | 123.28(19) |
| C(28B)—C(29B) | 1.522(7) | N(2B)—Mo(2)—C(18B) | 82.71(16) |
| C(28B)—C(30B) | 1.536(7) | C(16B)—Mo(2)—C(18B) | 54.77(17) |
| C(1T)—C(2T) | 1.376(7) | C(15B)—Mo(2)—C(18B) | 53.65(17) |
| C(1T)—C(6T) | 1.381(7) | C(17B)—Mo(2)—C(18B) | 32.59(15) |
| C(1T)—C(7T) | 1.496(7) | N(1B)—Mo(2)—N(3B) | 157.32(16) |
| C(2T)—C(3T) | 1.374(8) | C(1B)—Mo(2)—N(3B) | 91.72(18) |
| C(3T)—C(4T) | 1.372(8) | N(2B)—Mo(2)—N(3B) | 95.18(15) |
| C(4T)—C(5T) | 1.385(8) | C(16B)—Mo(2)—N(3B) | 55.84(16) |
| C(5T)—C(6T) | 1.381(7) | C(15B)—Mo(2)—N(3B) | 32.69(14) |
| N(1A)—Mo(1)—C(1A) | 99.5(2) | C(17B)—Mo(2)—N(3B) | 55.21(15) |
| N(1A)—Mo(1)—N(2A) | 96.24(16) | C(18B)—Mo(2)—N(3B) | 32.62(14) |
| C(1A)—Mo(1)—N(2A) | 98.82(19) | C(19A)—N(1A)—Mo(1) | 173.9(3) |
| N(1A)—Mo(1)—N(3A) | 99.65(17) | C(11A)—N(2A)—C(14A) | 105.8(4) |
| C(1A)—Mo(1)—N(3A) | 102.26(18) | C(11A)—N(2A)—Mo(1) | 131.2(3) |
| N(2A)—Mo(1)—N(3A) | 150.98(16) | C(14A)—N(2A)—Mo(1) | 121.2(3) |
| N(1A)—Mo(1)—N(3B) | 155.16(16) | C(15A)—N(3A)—C(18A) | 105.5(4) |
| C(1A)—Mo(1)—N(3B) | 105.19(18) | C(15A)—N(3A)—Mo(1) | 130.6(3) |
| N(2A)—Mo(1)—N(3B) | 77.85(14) | C(18A)—N(3A)—Mo(1) | 122.9(3) |
| N(3A)—Mo(1)—N(3B) | 77.54(14) | C(19B)—N(1B)—Mo(2) | 176.7(4) |
| N(1B)—Mo(2)—C(1B) | 100.5(2) | C(14B)—N(2B)—C(11B) | 105.7(4) |
| N(1B)—Mo(2)—N(2B) | 101.80(17) | C(14B)—N(2B)—Mo(2) | 122.4(3) |
| C(1B)—Mo(2)—N(2B) | 98.28(19) | C(11B)—N(2B)—Mo(2) | 130.4(4) |
| N(1B)—Mo(2)—C(16B) | 101.58(18) | C(15B)—N(3B)—C(18B) | 105.4(4) |
| C(1B)—Mo(2)—C(16B) | 113.26(19) | C(15B)—N(3B)—Mo(1) | 126.6(3) |
| N(2B)—Mo(2)—C(16B) | 136.06(17) | C(18B)—N(3B)—Mo(1) | 124.6(3) |
| N(1B)—Mo(2)—C(15B) | 128.59(18) | C(15B)—N(3B)—Mo(2) | 70.6(3) |
| C(1B)—Mo(2)—C(15B) | 86.18(19) | C(18B)—N(3B)—Mo(2) | 73.4(3) |
| Mo(1)—N(3B)—Mo(2) | 136.74(17) | C(20A)—C(25A)—C(27A) | 111.9(4) |
| C(2A)—C(1A)—Mo(1) | 145.1(4) | C(20A)—C(25A)—C(26A) | 110.2(4) |
| C(1A)—C(2A)—C(4A) | 111.2(4) | C(27A)—C(25A)—C(26A) | 110.3(4) |
| C(1A)—C(2A)—C(3A) | 106.5(4) | C(30A)—C(28A)—C(29A) | 109.5(5) |
| C(4A)—C(2A)—C(3A) | 108.6(4) | C(30A)—C(28A)—C(24A) | 114.9(5) |
| C(1A)—C(2A)—C(5A) | 108.6(4) | C(29A)—C(28A)—C(24A) | 110.1(5) |
| C(4A)—C(2A)—C(5A) | 109.7(4) | C(2B)—C(1B)—Mo(2) | 141.5(4) |
| C(3A)—C(2A)—C(5A) | 112.1(4) | C(1B)—C(2B)—C(5B) | 108.3(4) |
| C(10A)—C(5A)—C(6A) | 118.3(5) | C(1B)—C(2B)—C(3B) | 107.4(4) |
| C(10A)—C(5A)—C(2A) | 122.2(5) | C(5B)—C(2B)—C(3B) | 112.0(4) |
| C(6A)—C(5A)—C(2A) | 119.5(5) | C(1B)—C(2B)—C(4B) | 112.8(4) |
| C(7A)—C(6A)—C(5A) | 121.1(5) | C(5B)—C(2B)—C(4B) | 108.7(4) |
| C(8A)—C(7A)—C(6A) | 120.0(5) | C(3B)—C(2B)—C(4B) | 107.6(4) |
| C(7A)—C(8A)—C(9A) | 119.5(5) | C(6B)—C(5B)—C(10B) | 116.8(5) |
| C(8A)—C(9A)—C(10A) | 120.6(5) | C(6B)—C(5B)—C(2B) | 123.3(5) |
| C(5A)—C(10A)—C(9A) | 120.4(5) | C(10B)—C(5B)—C(2B) | 119.9(5) |
| C(12A)—C(11A)—N(2A) | 109.8(5) | C(7B)—C(6B)—C(5B) | 120.9(5) |
| C(11A)—C(12A)—C(13A) | 107.7(5) | C(8B)—C(7B)—C(6B) | 121.6(5) |
| C(14A)—C(13A)—C(12A) | 106.6(5) | C(7B)—C(8B)—C(9B) | 118.7(5) |
| C(13A)—C(14A)—N(2A) | 110.2(5) | C(8B)—C(9B)—C(10B) | 120.0(5) |
| N(3A)—C(15A)—C(16A) | 110.7(5) | C(9B)—C(10B)—C(5B) | 121.8(5) |
| C(15A)—C(16A)—C(17A) | 106.3(5) | C(12B)—C(11B)—N(2B) | 109.8(5) |
| C(18A)—C(17A)—C(16A) | 106.2(5) | C(11B)—C(12B)—C(13B) | 107.2(5) |
| C(17A)—C(18A)—N(3A) | 111.2(5) | C(14B)—C(13B)—C(12B) | 107.0(5) |
| N(1A)—C(19A)—C(24A) | 118.9(4) | C(13B)—C(14B)—N(2B) | 110.3(5) |
| N(1A)—C(19A)—C(20A) | 119.1(4) | N(3B)—C(15B)—C(16B) | 110.3(4) |
| C(24A)—C(19A)—C(20A) | 122.0(5) | N(3B)—C(15B)—Mo(2) | 76.7(3) |
| C(21A)—C(20A)—C(19A) | 117.5(5) | C(16B)—C(15B)—Mo(2) | 71.8(3) |
| C(21A)—C(20A)—C(25A) | 120.0(5) | C(15B)—C(16B)—C(17B) | 107.1(5) |
| C(19A)—C(20A)—C(25A) | 122.5(5) | C(15B)—C(16B)—Mo(2) | 74.2(3) |
| C(22A)—C(21A)—C(20A) | 121.0(5) | C(17B)—C(16B)—Mo(2) | 76.3(3) |
| C(21A)—C(22A)—C(23A) | 120.9(5) | C(18B)—C(17B)—C(16B) | 106.0(5) |
| C(24A)—C(23A)—C(22A) | 121.0(5) | C(18B)—C(17B)—Mo(2) | 74.3(3) |
| C(23A)—C(24A)—C(19A) | 117.5(5) | C(16B)—C(17B)—Mo(2) | 69.8(3) |
| C(23A)—C(24A)—C(28A) | 121.0(5) | C(17B)—C(18B)—N(3B) | 111.1(4) |
| C(19A)—C(24A)—C(28A) | 121.5(5) | C(17B)—C(18B)—Mo(2) | 73.1(3) |
| N(3B)—C(18B)—Mo(2) | 74.0(3) | | |
| N(1B)—C(19B)—C(24B) | 118.7(5) | | |
| N(1B)—C(19B)—C(20B) | 119.5(5) | | |
| C(24B)—C(19B)—C(20B) | 121.7(5) | | |
| C(21B)—C(20B)—C(19B) | 117.7(5) | | |
| C(21B)—C(20B)—C(25B) | 121.9(5) | | |
| C(19B)—C(20B)—C(25B) | 120.3(4) | | |
| C(22B)—C(21B)—C(20B) | 121.4(5) | | |
| C(21B)—C(22B)—C(23B) | 120.6(5) | | |
| C(22B)—C(23B)—C(24B) | 120.8(5) | | |
| C(23B)—C(24B)—C(19B) | 117.7(5) | | |

TABLE 5-continued

Bond lengths [Å] and angles [°] for {Mo(NAr)(CHR)(NC$_4$H$_4$)$_2$}$_2$.

| | |
|---|---|
| C(23B)—C(24B)—C(28B) | 120.2(5) |
| C(19B)—C(24B)—C(28B) | 122.1(5) |
| C(20B)—C(25B)—C(26B) | 114.4(4) |
| C(20B)—C(25B)—C(27B) | 108.3(4) |
| C(26B)—C(25B)—C(27B) | 110.3(5) |
| C(24B)—C(28B)—C(29B) | 111.7(4) |
| C(24B)—C(28B)—C(30B) | 110.7(4) |
| C(29B)—C(28B)—C(30B) | 110.4(4) |
| C(2T)—C(1T)—C(6T) | 117.9(5) |
| C(2T)—C(1T)—C(7T) | 120.9(5) |
| C(6T)—C(1T)—C(7T) | 121.2(5) |
| C(3T)—C(2T)—C(1T) | 121.3(6) |
| C(4T)—C(3T)—C(2T) | 120.9(6) |
| C(3T)—C(4T)—C(5T) | 118.5(6) |
| C(6T)—C(5T)—C(4T) | 120.3(5) |
| C(1T)—C(6T)—C(5T) | 121.2(5) |

TABLE 6

Anisotropic displacement parameters (Å$^2$ × 10$^3$) for {Mo(NAr)(CHR)(NC$_4$H$_4$)$_2$}$_2$. The anisotropic displacement factor exponent takes the form: $-2\pi^2[h^2 a^{*2}U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| Mo(1) | 15(1) | 15(1) | 15(1) | 0(1) | 1(1) | 1(1) |
| Mo(2) | 14(1) | 15(1) | 18(1) | −1(1) | 2(1) | 0(1) |
| N(1A) | 15(2) | 14(3) | 13(2) | 2(2) | 2(2) | 0(2) |
| N(2A) | 13(2) | 17(3) | 18(3) | 3(2) | −2(2) | 2(2) |
| N(3A) | 14(2) | 12(3) | 18(3) | −1(2) | 0(2) | 4(2) |
| N(1B) | 15(3) | 20(3) | 11(2) | 5(2) | 0(2) | 0(2) |
| N(2B) | 18(2) | 16(3) | 19(3) | −3(2) | 6(2) | 0(2) |
| N(3 B) | 19(3) | 12(3) | 18(3) | −3(2) | 1(2) | −1(2) |
| C(1A) | 17(3) | 19(3) | 13(3) | 2(2) | 1(2) | 6(2) |
| C(2A) | 21(3) | 20(3) | 21(3) | 5(3) | 3(3) | 1(3) |
| C(3 A) | 38(4) | 25(3) | 28(3) | 5(3) | 17(3) | 1(3) |
| C(4A) | 21(3) | 25(3) | 32(4) | 5(3) | 6(3) | −1(3) |
| C(5A) | 9(3) | 20(3) | 24(3) | −3(3) | 7(2) | −6(2) |
| C(6A) | 22(3) | 26(4) | 25(3) | 2(3) | 11(3) | −2(3) |
| C(7A) | 28(4) | 23(4) | 29(4) | −6(3) | 9(3) | −1(3) |
| C(8A) | 22(3) | 17(3) | 47(4) | 11(3) | 14(3) | 3(3) |
| C(9A) | 22(3) | 34(4) | 21(3) | 17(3) | 5(3) | 2(3) |
| C(10A) | 23(3) | 31(4) | 17(3) | 9(3) | 6(3) | 2(3) |
| C(11A) | 15(3) | 24(4) | 24(4) | 0(3) | 4(3) | −2(3) |
| C(12A) | 25(3) | 25(4) | 24(4) | −9(3) | 5(3) | −4(3) |
| C(13A) | 23(3) | 14(3) | 37(4) | −4(3) | 4(3) | −2(3) |
| C(14A) | 16(3) | 27(4) | 22(3) | 7(3) | 3(3) | 8(3) |
| C(15A) | 14(3) | 16(3) | 18(3) | −2(2) | −1(2) | −1(2) |
| C(16A) | 24(3) | 16(3) | 19(3) | −8(3) | −2(3) | 5(3) |
| C(17A) | 20(3) | 37(4) | 15(3) | −5(3) | 5(3) | 3(3) |
| C(18A) | 21(3) | 24(3) | 19(3) | 3(3) | 5(3) | 0(3) |
| C(19A) | 12(3) | 18(3) | 17(3) | 4(3) | 1(3) | −1(2) |
| C(20A) | 18(3) | 21(3) | 30(4) | 2(3) | 11(3) | −3(3) |
| C(21A) | 17(3) | 25(3) | 32(4) | 6(3) | 6(3) | 4(3) |
| C(22A) | 12(3) | 34(4) | 35(4) | 9(3) | −1(3) | −2(3) |
| C(23A) | 20(3) | 35(4) | 25(3) | 2(3) | −3(3) | −3(3) |
| C(24A) | 16(3) | 26(4) | 26(4) | 5(3) | 5(3) | −4(3) |
| C(25A) | 19(3) | 25(3) | 28(4) | 0(3) | 9(3) | 5(3) |
| C(26A) | 27(3) | 38(4) | 29(4) | −6(3) | 9(3) | 4(3) |
| C(27A) | 30(4) | 30(4) | 41(4) | −7(3) | 8(3) | 4(3) |
| C(28A) | 23(3) | 43(4) | 26(4) | −8(3) | −7(3) | 5(3) |
| C(29A) | 99(4) | 47(3) | 44(3) | 1(3) | 44(3) | 13(3) |
| C(30A) | 99(4) | 47(3) | 44(3) | 1(3) | 44(3) | 13(3) |
| C(1B) | 17(3) | 15(3) | 26(3) | −2(3) | 4(2) | 0(2) |
| C(2B) | 16(3) | 24(3) | 23(3) | 6(3) | 7(3) | 0(3) |
| C(3B) | 37(4) | 21(3) | 31(4) | 2(3) | 12(3) | −4(3) |
| C(4B) | 24(3) | 24(3) | 22(3) | −3(3) | −1(3) | 1(3) |
| C(5B) | 13(3) | 14(3) | 24(3) | 8(3) | 1(3) | 9(3) |
| C(6B) | 21(3) | 25(3) | 25(3) | 1(3) | 6(3) | −3(3) |
| C(7B) | 19(3) | 23(3) | 35(4) | −6(3) | −7(3) | −5(3) |
| C(8B) | 28(4) | 26(4) | 23(3) | −2(3) | 3(3) | 2(3) |
| C(9B) | 22(3) | 32(4) | 20(3) | −1(3) | 2(3) | 3(3) |
| C(10B) | 14(3) | 18(3) | 33(4) | 2(3) | 4(3) | −6(2) |
| C(11B) | 22(3) | 23(3) | 31(4) | 6(3) | 13(3) | −2(3) |
| C(12B) | 27(3) | 34(4) | 28(4) | 1(3) | 17(3) | −4(3) |
| C(13B) | 28(3) | 29(4) | 18(3) | −6(3) | 4(3) | 2(3) |
| C(14B) | 18(3) | 17(3) | 23(3) | −3(3) | 2(3) | −1(2) |
| C(15B) | 22(3) | 20(3) | 17(3) | 0(2) | 4(3) | 8(3) |
| C(16B) | 19(3) | 23(3) | 15(3) | 0(3) | 9(3) | 0(3) |
| C(17B) | 13(3) | 19(3) | 18(3) | 2(3) | −1(2) | 1(2) |
| C(18B) | 17(3) | 17(3) | 18(3) | 0(2) | 0(3) | 4(2) |
| C(19B) | 21(3) | 6(3) | 21(3) | −1(2) | 1(3) | 2(2) |
| C(20B) | 18(3) | 10(3) | 25(3) | −6(2) | 3(3) | 3(2) |
| C(21B) | 21(3) | 22(3) | 24(4) | −2(3) | 8(3) | −3(3) |
| C(22B) | 15(3) | 18(3) | 30(4) | −2(3) | 0(3) | −1(2) |
| C(23B) | 31(4) | 25(4) | 17(3) | 0(3) | 0(3) | −6(3) |
| C(24B) | 18(3) | 15(3) | 20(3) | 1(2) | 2(3) | −4(2) |
| C(25B) | 12(3) | 31(4) | 19(3) | −8(3) | 0(2) | 5(3) |
| C(26B) | 35(4) | 53(4) | 25(4) | −11(3) | 6(3) | 8(3) |
| C(27B) | 29(4) | 36(4) | 18(3) | 7(3) | 3(3) | −6(3) |
| C(28B) | 19(3) | 27(3) | 14(3) | 1(3) | −3(2) | −7(3) |
| C(29B) | 43(4) | 34(4) | 19(3) | 1(3) | 12(3) | −4(3) |
| C(30B) | 23(3) | 31(4) | 23(3) | 2(3) | 2(3) | 0(3) |
| C(1T) | 25(4) | 28(4) | 21(3) | 6(3) | 3(3) | 0(3) |
| C(2T) | 26(4) | 44(4) | 20(3) | 2(3) | 4(3) | −12(3) |
| C(3T) | 25(4) | 52(5) | 31(4) | 3(3) | 7(3) | 8(3) |
| C(4T) | 42(4) | 37(4) | 23(3) | 4(3) | 11(3) | 13(3) |
| C(5T) | 36(4) | 30(4) | 23(3) | 5(3) | 8(3) | −5(3) |
| C(6T) | 19(3) | 30(4) | 28(3) | 4(3) | 7(3) | 3(3) |
| C(7T) | 47(4) | 26(4) | 38(4) | 5(3) | 12(3) | −5(3) |

TABLE 7

Hydrogen coordinates (×10$^4$) and isotropic displacement parameters (Å$^2$ × 10$^3$) for {Mo(NAr)(CHR)(NC$_4$H$_4$)$_2$}$_2$.

| | x | y | z | U(eq) |
|---|---|---|---|---|
| H(10B) | 2855 | 10063 | 3872 | 20 |
| H(10C) | 3369 | 9623 | 2878 | 43 |
| H(10D) | 3820 | 8899 | 3417 | 43 |
| H(10E) | 4018 | 9918 | 3071 | 43 |
| H(11C) | 4184 | 10700 | 4880 | 39 |
| H(11D) | 4511 | 10573 | 4281 | 39 |
| H(11E) | 4314 | 9552 | 4629 | 39 |
| H(57A) | 3579 | 11962 | 4681 | 28 |
| H(25A) | 3386 | 13723 | 4385 | 32 |
| H(44A) | 3175 | 14258 | 3192 | 34 |
| H(19A) | 3113 | 13009 | 2296 | 31 |
| H(39A) | 3344 | 11255 | 2592 | 28 |
| H(58A) | 2807 | 7886 | 3099 | 25 |

TABLE 7-continued

Hydrogen coordinates (×10$^4$) and isotropic displacement parameters
(Å$^2$ × 10$^3$) for {Mo(NAr)(CHR)(NC$_4$H$_4$)$_2$}$_2$.

| | x | y | z | U(eq) |
|---|---|---|---|---|
| H(17A) | 2543 | 6029 | 2802 | 30 |
| H(9A) | 2634 | 5062 | 3960 | 30 |
| H(50A) | 2955 | 6357 | 4945 | 27 |
| H(28A) | 2690 | 11330 | 5083 | 20 |
| H(15A) | 2252 | 11831 | 6039 | 26 |
| H(10L) | 2236 | 10175 | 6781 | 28 |
| H(11A) | 2672 | 8757 | 6252 | 26 |
| H(10F) | 5280 | 6704 | 5734 | 30 |
| H(10A) | 5570 | 7248 | 6910 | 34 |
| H(10K) | 5055 | 8465 | 7352 | 34 |
| H(27A) | 4017 | 7529 | 4433 | 28 |
| H(61A) | 4871 | 8256 | 4333 | 47 |
| H(61B) | 4683 | 7296 | 3787 | 47 |
| H(61C) | 5167 | 7134 | 4515 | 47 |
| H(10H) | 3997 | 5788 | 4860 | 50 |
| H(10I) | 4629 | 5616 | 4841 | 50 |
| H(10J) | 4147 | 5784 | 4111 | 50 |
| H(8A) | 3697 | 9403 | 6426 | 40 |
| H(20B) | 4091 | 11058 | 6811 | 88 |
| H(20C) | 4264 | 10663 | 6120 | 88 |
| H(20D) | 4701 | 10588 | 6896 | 88 |
| H(48A) | 3868 | 9852 | 7630 | 88 |
| H(48B) | 4475 | 9327 | 7804 | 88 |
| H(48C) | 3928 | 8609 | 7549 | 88 |
| H(46A) | 1943 | 10649 | 3805 | 23 |
| H(12A) | 2150 | 12128 | 3113 | 44 |
| H(12B) | 1664 | 12928 | 2729 | 44 |
| H(12C) | 1671 | 11763 | 2421 | 44 |
| H(65A) | 542 | 11688 | 3216 | 37 |
| H(65B) | 702 | 11499 | 2482 | 37 |
| H(65C) | 699 | 12665 | 2790 | 37 |
| H(22A) | 2138 | 13367 | 3911 | 28 |
| H(91A) | 2239 | 14364 | 4934 | 35 |
| H(52A) | 1689 | 14067 | 5696 | 32 |
| H(81A) | 1038 | 12698 | 5443 | 31 |
| H(86A) | 929 | 11697 | 4417 | 27 |
| H(24A) | 1988 | 10030 | 2290 | 29 |
| H(10G) | 2020 | 8948 | 1248 | 34 |
| H(80A) | 1582 | 7186 | 1376 | 31 |
| H(54A) | 1273 | 7257 | 2474 | 24 |
| H(11F) | 1755 | 9717 | 5047 | 24 |
| H(55A) | 839 | 8696 | 4726 | 22 |
| H(11G) | 970 | 7075 | 3981 | 21 |
| H(11B) | 1952 | 7195 | 3831 | 22 |
| H(45A) | −1213 | 10197 | 2784 | 26 |
| H(20A) | −1442 | 10263 | 1550 | 27 |
| H(41A) | −771 | 9965 | 950 | 31 |
| H(26A) | 143 | 9915 | 3963 | 26 |
| H(90A) | −598 | 11048 | 4028 | 57 |
| H(90B) | −496 | 10170 | 4640 | 57 |
| H(90C) | −1011 | 10062 | 3937 | 57 |
| H(71A) | −37 | 8115 | 3668 | 43 |
| H(71B) | −666 | 8251 | 3707 | 43 |
| H(71C) | −159 | 8371 | 4417 | 43 |
| H(78A) | 690 | 9456 | 1795 | 26 |
| H(83A) | 452 | 11105 | 1239 | 47 |
| H(83B) | 5 | 10554 | 586 | 47 |
| H(83C) | 657 | 10323 | 718 | 47 |
| H(31A) | 169 | 7937 | 1313 | 40 |
| H(31B) | 486 | 8388 | 764 | 40 |
| H(31C) | −168 | 8597 | 629 | 40 |
| H(2TA) | 5656 | 4024 | 3438 | 37 |
| H(3TA) | 5359 | 5660 | 3693 | 43 |
| H(4TA) | 5983 | 7059 | 3986 | 40 |
| H(5TA) | 6920 | 6779 | 4021 | 36 |
| H(6TA) | 7220 | 5121 | 3794 | 31 |
| H(7TA) | 7060 | 3354 | 3471 | 55 |
| H(7TB) | 6456 | 3131 | 2935 | 55 |
| H(7TC) | 6582 | 2826 | 3764 | 55 |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:
1. A method for synthesizing a catalyst, comprising:
providing a compound having the structure of formula I:

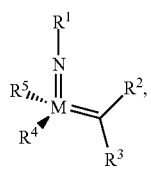

wherein:
M is Mo or W;
$R^1$ is alkyl, heteroalkyl, aryl, or heteroaryl, optionally substituted;
$R^2$ and $R^3$ can be the same or different and are hydrogen, alkyl, heteroalkyl, aryl, or heteroaryl, optionally substituted;
$R^4$ and $R^5$ can be the same or different and are heteroaryl, optionally substituted, or $R^4$ and $R^5$ are joined together to form a bidentate ligand with respect to M, optionally substituted; and wherein $R^4$ and $R^5$ each comprise at least one nitrogen atom; and
reacting the compound with an oxygen-containing ligand such that the oxygen-containing ligand replaces $R^4$ and $R^5$ to form a catalyst.
2. A method as in claim 1, wherein $R^4$ and $R^5$ each coordinate M via a nitrogen atom.
3. A method as in claim 1, wherein the oxygen-containing ligand is a bidentate ligand.
4. A method as in claim 1, wherein the oxygen-containing ligand is a chiral ligand.
5. A method as in claim 1, wherein the oxygen-containing ligand is attached to a surface via a covalent or a non-covalent bond.
6. A method as in claim 1, wherein $R^4$ and $R^5$ are each pyrrolyl, optionally substituted, and coordinate M via the nitrogen atom of the pyrrolyl ring.
7. A method as in claim 1, wherein $R^1$ is substituted phenyl.
8. A method as in claim 1, wherein $R^1$ is adamantyl, optionally substituted.
9. A method as in claim 1, wherein the oxygen-containing ligand is a hydroxy-substituted aryl group, wherein the hydroxyl group is deprotonated upon coordination to the metal center.
10. A method as in claim 1, wherein the oxygen-containing ligand is monoalcohol, wherein the hydroxyl group is deprotonated upon coordination to the metal center.
11. A method as in claim 6, wherein $R^4$ and $R^5$ are each pyrrolyl.
12. A method as in claim 7, wherein $R^1$ is 2,6-dialkylphenyl.
13. A method as in claim 1, further comprising,
catalyzing a reaction with the catalyst, wherein the catalyst is present at a concentration of less than 100 mM.
14. A method as in claim 13, wherein the reaction is a carbon-carbon bond forming reaction.
15. A method as in claim 13, wherein the reaction is an olefin metathesis reaction.
16. A method as in claim 13, wherein the olefin metathesis reaction is a ring-closing reaction, a ring-opening reaction, or a cross-metathesis reaction.
17. A method as in claim 1, wherein the catalyst has the structure:

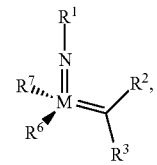

wherein:
M is Mo or W;
$R^1$ is alkyl, heteroalkyl, aryl, or heteroaryl, optionally substituted;
$R^2$ and $R^3$ can be the same or different and are hydrogen, alkyl, heteroalkyl, aryl, or heteroaryl, optionally substituted;
$R^6$ and $R^7$ can be the same or different and are heteroalkyl or heteroaryl, optionally substituted, or $R^6$ and $R^7$ are joined together to form a bidentate ligand with respect to M, optionally substituted; and
wherein $R^6$ and $R^7$ each comprise at least one oxygen atom.
18. A method as in claim 17, wherein M is Mo.
19. A method as in claim 17, wherein $R^6$ and $R^7$ each coordinate M via an oxygen atom.
20. A method as in claim 17, wherein $R^6$ and $R^7$ are joined together to form a biphenolate or binaptholate ligand.
21. A method as in claim 17, wherein $R^6$ and $R^7$ are joined together to form a chiral ligand.
22. A method as in claim 1, comprising
providing in a reaction vessel a compound having the structure:

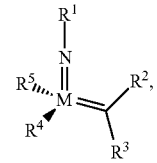

wherein:
M is Mo or W;
$R^1$ is alkyl, heteroalkyl, aryl, or heteroaryl, optionally substituted;

$R^2$ and $R^3$ can be the same or different and are hydrogen, alkyl, heteroalkyl, aryl, or heteroaryl, optionally substituted;

$R^4$ and $R^5$ can be the same or different and are heteroaryl, optionally substituted, or $R^4$ and $R^5$ are joined together to form a bidentate ligand with respect to M, optionally substituted; and wherein $R^4$ and $R^5$ each comprise at least one nitrogen atom; and reacting in the reaction vessel the compound with an oxygen-containing ligand such that the oxygen-containing ligand replaces $R^4$ and $R^5$ to form a catalyst; and catalyzing a reaction in the reaction vessel with the catalyst.

23. A method as in claim 22, wherein the reaction is an olefin metathesis reaction.

24. A method as in claim 22, wherein the catalyst has the structure:

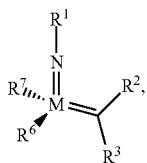

wherein:
M is Mo or W;
$R^1$ is alkyl, heteroalkyl, aryl, or heteroaryl, optionally substituted;
$R^2$ and $R^3$ can be the same or different and are hydrogen, alkyl, heteroalkyl, aryl, or heteroaryl, optionally substituted;
$R^6$ and $R^7$ can be the same or different and are heteroalkyl or heteroaryl, optionally substituted, or $R^6$ and $R^7$ are joined together to form a bidentate ligand with respect to M, optionally substituted; and
wherein $R^6$ and $R^7$ each comprise at least one oxygen atom.

25. A method for synthesizing a metal complex, comprising:
providing a compound having the structure of formula I:

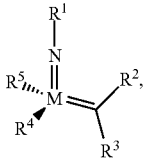

wherein:
M is Mo or W;
$R^1$ is alkyl, heteroalkyl, aryl, or heteroaryl, optionally substituted;
$R^2$ and $R^3$ can be the same or different and are hydrogen, alkyl, heteroalkyl, aryl, or heteroaryl, optionally substituted;
$R^4$ and $R^5$ can be the same or different and are heteroalkyl or heteroaryl, optionally substituted, or $R^4$ and $R^5$ are joined together to form a bidentate ligand with respect to M, optionally substituted; and wherein $R^4$ and $R^5$ each comprise at least one nitrogen atom; and reacting the compound with an oxygen-containing ligand such that the oxygen-containing ligand replaces $R^4$ and $R^5$; wherein:

$R^4$ and $R^5$ each coordinate M via nitrogen;
the oxygen-containing ligand coordinates M via oxygen; and
the compound having the structure of formula I is other than:
Mo(NAr)(CHR')(NPh$_2$)$_2$,
Mo(NAr')(CHCMe$_2$Ph)(NPh$_2$)$_2$,
Mo(NAr)(CHR')[N(t-Bu)(3,5-C$_6$H$_3$Me$_2$)]$_2$, and
Mo(NAr)(CHR')[N(i-Pr)(3,5-C$_6$H$_3$Me$_2$)]$_2$,
wherein R' is t-Bu or CMe$_2$Ph, Ar 2,6-i-Pr$_2$C$_6$H$_3$, and Ar'=2,6-Me$_2$C$_6$H$_3$.

26. A method as in claim 25, wherein $R^1$ is alkyl, heteroalkyl, aryl, or heteroaryl, optionally substituted.

27. A method as in claim 25, wherein $R^1$ is not 2,6-dialkylphenyl.

28. A method as in claim 25, wherein $R^4$ and $R^5$ can be the same or different and are pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, optionally substituted.

29. A method for synthesizing a metal complex, comprising:
providing a compound having the structure of formula I:

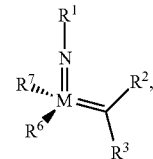

wherein:
M is Mo or W;
$R^1$ is alkyl, heteroalkyl, aryl, or heteroaryl, optionally substituted;
$R^2$ and $R^3$ can be the same or different and are hydrogen, alkyl, heteroalkyl, aryl, or heteroaryl, optionally substituted;
$R^4$ and $R^5$ can be the same or different and are heteroalkyl or heteroaryl, optionally substituted, or $R^4$ and $R^5$ are joined together to form a bidentate ligand with respect to M, optionally substituted; and wherein $R^4$ and $R^5$ each comprise at least one nitrogen atom; and reacting the compound with an oxygen-containing ligand such that the oxygen-containing ligand replaces $R^4$ and $R^5$, wherein:
$R^4$ and $R^5$ each coordinate M via nitrogen;
the oxygen-containing coordinates M via oxygen; and
the oxygen-containing ligand is monodentate, and is other than Me$_3$CO— and (CF$_3$)$_2$MeCO—.

30. A method as in claim 29, wherein the oxygen atom via which the oxygen-containing ligand coordinates M is positioned on a substituent of an alkyl, heteroalkyl, aryl, or heteroaryl group.

31. A method as in claim 29, wherein the oxygen-containing ligand is a hydroxy-substituted aryl group, wherein the hydroxyl group is deprotonated upon coordination to the metal center.

32. A method as in claim 29, wherein $R^4$ and $R^5$ can be the same or different and are optionally substituted heteroaryl comprising at least one nitrogen ring atom, wherein $R^4$ and $R^5$ coordinate M via the nitrogen ring atom.

* * * * *